United States Patent [19]

Sukesada et al.

[11] Patent Number: 5,972,648
[45] Date of Patent: Oct. 26, 1999

[54] HIRUDIN ANALOGS, METHODS OF MANUFACTURE THEREOF AND ANTICOAGULANT COMPOSITIONS HAVING THESE AS ACTIVE INGREDIENTS

[75] Inventors: Akiko Sukesada, Urawa; Satoru Misawa, Tokyo; Hitoshi Matsuda, Saitama, all of Japan

[73] Assignee: Japan Energy Corporation, Tokyo, Japan

[21] Appl. No.: 08/861,459

[22] Filed: May 22, 1997

Related U.S. Application Data

[63] Continuation of application No. 08/244,361, filed as application No. PCT/JP93/01384, Sep. 28, 1993, abandoned.

[51] Int. Cl.[6] ........................ C07H 21/04; C12N 15/12; C12N 15/63; C07K 14/00
[52] U.S. Cl. ................. 435/69.1; 536/23.1; 435/320.1; 435/325; 435/252.3; 435/172.3; 530/324; 514/2
[58] Field of Search .............................. 435/69.1, 302.1, 435/325, 253.3, 172.3; 530/324; 514/2; 536/23.1

[56] References Cited

U.S. PATENT DOCUMENTS

| | | | |
|---|---|---|---|
| 5,118,790 | 6/1992 | Winant et al. | 530/324 |
| 5,126,134 | 6/1992 | Heim et al. | 424/94.64 |
| 5,192,745 | 3/1993 | Krstenansky et al. | 514/9 |
| 5,192,747 | 3/1993 | Krstenansky et al. | 514/15 |
| 5,204,323 | 4/1993 | Findlay | 514/2 |

FOREIGN PATENT DOCUMENTS

| | | |
|---|---|---|
| 171024 A | 2/1986 | European Pat. Off. . |
| 0 365 468 | 4/1990 | European Pat. Off. . |
| 367713 | 5/1990 | European Pat. Off. . |
| 412526 | 2/1991 | European Pat. Off. . |
| 468448 | 1/1992 | European Pat. Off. . |
| 511393 | 11/1992 | European Pat. Off. . |
| 2-121934 | of 1990 | Japan . |
| 2-145526 | of 1990 | Japan . |
| 4-173798 | 6/1992 | Japan . |
| 5068582 | 3/1993 | Japan . |
| 5-310-788 | 11/1993 | Japan . |
| 5310788 | 11/1993 | Japan . |
| 8603517 | 6/1986 | WIPO . |
| 9117250 | 11/1991 | WIPO . |
| 9304082 | 3/1993 | WIPO . |
| 9408034 | 4/1994 | WIPO . |

OTHER PUBLICATIONS

Payne et al. (1991), "Positional Effects of Sulfation in Hirudin and Hirudin PA Related Anticoagulant Peptides," 34 *J. Medicinal Chem.* 1184–1187.

Broersma et al. (1991), "Antithrombotic Activity of a Novel C–Terminal Hirudin Analog in Experimental Animals," 65 *Thrombosis & Haemostasis* 377–381.

Lehman et al. (1993), "Expression, Purification and Characterization of Multigram Amounts of a Recombinant Hybrid HV1–HV2 Hirudin Variant Expressed in *Saccharomyces cerevisiae*," 4 *Protein Expr. & Purif.* 247–255.

Komatsu et al. (1993), "CX–397, A Novel Recombinant Hirudin Analog Having a Hybrid Sequence of Hirudin Variants–1 and –3,," 196 *Biochem. & Biophys. Res. Comm.* 773–779.

*Primary Examiner*—Lila Feisee
*Assistant Examiner*—Nirmal S. Basi
*Attorney, Agent, or Firm*—Testa, Hurwitz & Thibeault, LLP

[57] ABSTRACT

Disclosed are hirudin analogs, a method of manufacture thereof, and anticoagulant compositions containing the same. Sequences $Asp^{33}$-$Gly^{34}$ or $Asp^{62}$-$Ala^{63}$ of naturally-occurring hirudins or their analogs were substituted as disclosed to suppress the formation of succinimide- or beta-forms, thereby yielding hirudin analogs with high stability, high anti-thrombin activity, and therapeutic potential as anticoagulants. Hirudin analogs having $Val^1$-$Val^2$ of naturally-occurring hirudin substituted with $Ile^1$-$Ile^2$ are preferred for their high antithrombiin activity. The invention also provides DNAs encoding the amino acid sequence of hirudin analogs, expression vectors, recombinant microogranisms, and a method of manufacturing hirudin analogs using recombinant microorganisms.

19 Claims, 11 Drawing Sheets

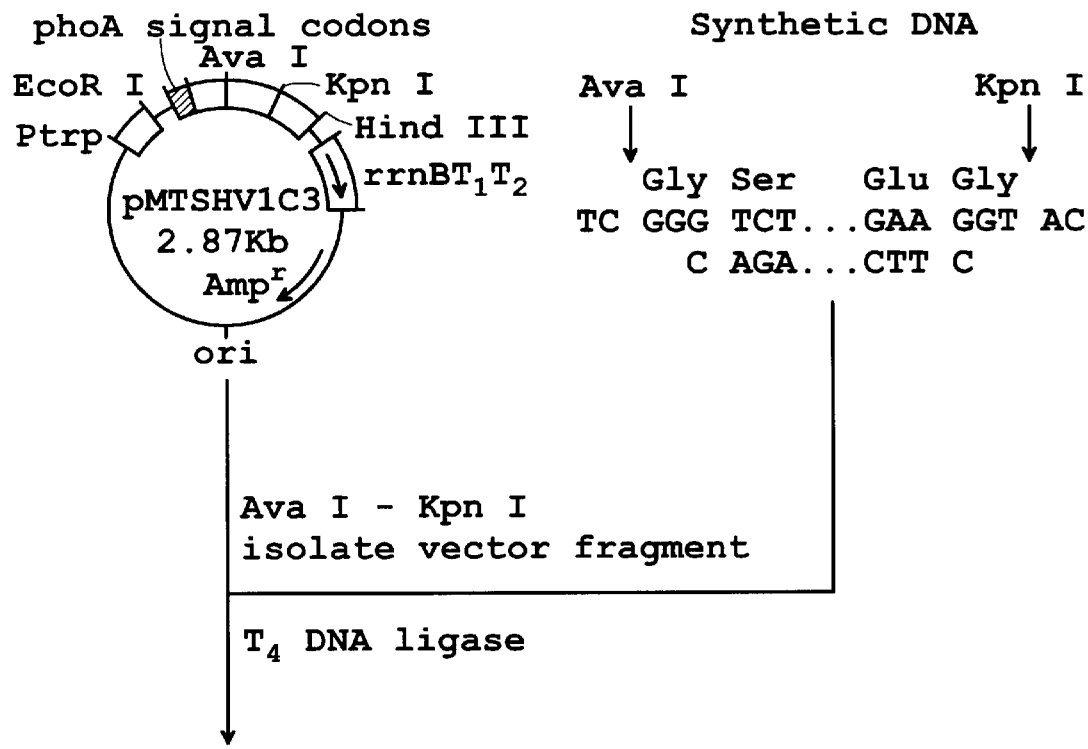
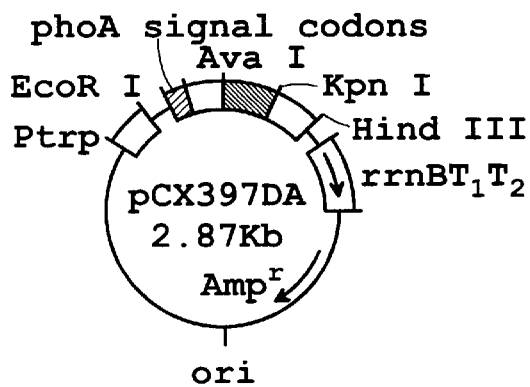
FIG. 1

```
            31                    35                        40
        Gly Ser Asp Ala Glu Lys Asn Gln Cys Val
   ⌐TC  GGG TCT GAT GCT GAA AAG AAC CAG TGT GTT
   └─┐C  AGA CTA CGA CTT TTC TTG GTC ACA CAA
     Ava I

44
   Thr Gly Glu Gly
   ACT GGT GAA GGT AC⌐         DA-1
   TGA CCA CTT C   └─┐         DA-2
              Kpn I
                 (A)

31                    35                        40
        Gly Ser Asn Ala Glu Lys Asn Gln Cys Val
   ⌐TC  GGG TCT AAC GCT GAA AAG AAC CAG TGT GTT
   └─┐C  AGA TTG CGA CTT TTC TTG GTC ACA CAA
     Ava I

44
   Thr Gly Glu Gly
   ACT GGT GAA GGT AC⌐         NA-1
   TGA CCA CTT C   └─┐         NA-2
              Kpn I
                 (B)
```

FIG. 2

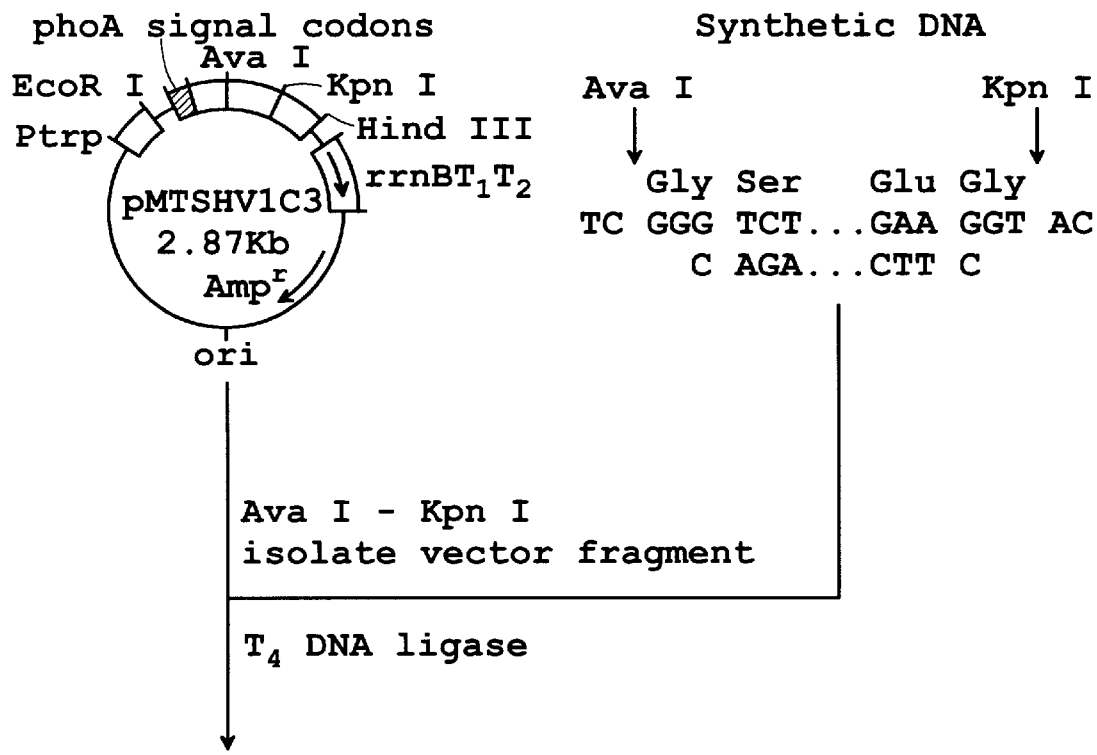
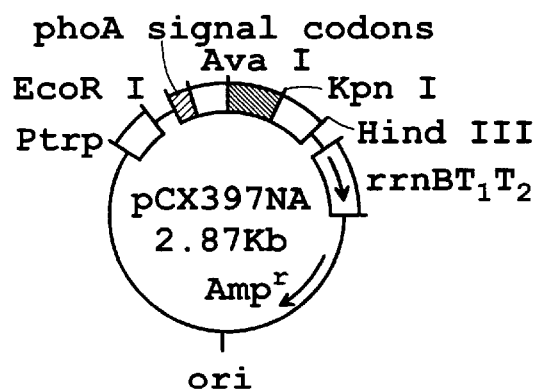
FIG. 3

```
                                    50                      55
       Pro Lys Pro Gln Ser His Asn Gln Gly Asp Phe
    ┌─┐C CCG AAA CCG CAG TCT CAT AAC CAG GGT GAT TTC  1-1
    │CA TGG GGC TTT GGC GTC AGA GTA TTG GTC CCA CTA AAG
    │                    1-3
Kpn I
           60                 65
Glu Pro Ile Pro Glu Glu Ala Tyr Asp Glu
GAA CCG ATC CCG GAA GAA GCG TAC GAT GAA TAA A┐          1-2
CTT GGC TAG│GGC CTT CTT CGC ATG CTA CTT ATT TTC GA│
           1-4                                   Hind III
                            (1)

50                      55
       Pro Lys Pro Gln Ser His Asn Gln Gly Asp Phe
    ┌─┐C CCG AAA CCG CAG TCT CAT AAC CAG GGT GAT TTC  2-1
    │CA TGG GGC TTT GGC GTC AGA GTA TTG GTC CCA CTA AAG
    │                    2-3
Kpn I
           60                 65
Glu Pro Ile Pro Glu Asp Tyr Asp Glu
GAA CCG ATC CCG GAA GAC TAC GAT GAA TAA A┐              2-2
CTT GGC TAG│GGC CTT CTG ATG CTA CTT ATT TTC GA│
           2-4                               Hind III
                            (2)

50                      55
       Pro Lys Pro Gln Ser His Asn Gln Gly Asp Phe
    ┌─┐C CCG AAA CCG CAG TCT CAT AAC CAG GGT GAT TTC  3-1
    │CA TGG GGC TTT GGC GTC AGA GTA TTG GTC CCA CTA AAG
    │                    3-3
Kpn I
           60                 65
Glu Pro Ile Pro Glu Asp Tyr Leu Asp Glu
GAA CCG ATC CCG GAA GAC TAC CTG GAC GAA TAA A┐          3-2
CTT GGC TAG│GGC CTT CTG ATG GAC CTG CTT ATT TTC GA│
           3-4                                   Hind III
                            (3)
```

FIG. 6

HIRUDIN ANALOGS, METHODS OF MANUFACTURE THEREOF AND ANTICOAGULANT COMPOSITIONS HAVING THESE AS ACTIVE INGREDIENTS

This is a continuation of copending application Ser. No. 08/244,361 filed Dec. 12, 1994, U.S. National phase of International Application PCT/JP 93/01384 filed on Sep. 28, 1993 and which designated the U.S.

TECHNICAL FIELD

The present invention concerns novel hirudin analogs, the amino acids sequences of which differ from those of natural hirudin analogs. The present invention also relates to the DNAs which provide the sequence code for the above-mentioned novel polypeptides.

Furthermore, the present invention concerns vectors used to express the above-mentioned novel hirudin analogs, recombinant *E. coli* transformed by the expression vectors, and a method of producing the hirudin analogs through a secretion approach by amplifying transformed *E. coli*.

Finally, the present invention concerns anticoagulants containing at least one novel hirudin analog with the above-mentioned novel amino acid sequence as their active ingredient.

BACKGROUND ART

Hirudin is a polypeptide with anti-thrombotic activity which is isolated from the salivary glands of the medicinal leech, *Hirudo medicinalis*. Three hirudin analogs, HV1, HV2 and HV3 are known as natural hirudins. The amino acid sequence of these natural hirudins has been identified. The genes coding the identified amino acid sequence been cloned as c-DNAs, and the DNA sequences have also been identified.

Expression vectors were prepared using the c-DNAs cloned from natural genes. Expression of the polypeptides, the hirudin analogs, has been carried out by introducing the expression vectors into host microorganisms such as *E. coli* (*Escherichia coli*) and yeast (*Saccharomyces cerevisiae*).

Furthermore, based on knowledge related to the amino acid sequences of the natural hirudins, hirudin analogs with an artificial mutation of the amino acid sequence have been produced. The following are reported as examples. HV2 (Lys$^{47}$) was made by introducing one amino acid substitution into the natural hirudin HV2. This hirudin analog exhibited an increased antithrombin activity as compared with that of the natural hirudin HV2, and exhibited a high antithrombin activity equivalent to that of the natural hirudin HV1. Other examples include an analog of the natural hirudin HV1 in which the amino acid sequence of the N-terminal region was substituted with other amino acids, and the HV1-like analog having extra amino acids attached to its N-terminal. An analog made by replacing the amino acid sequence of the N-terminal of natural hirudin HV1 from Val$^1$-Val$^2$- to Ile$^2$-Ile$^2$- was reported to exhibit a higher antithrombin activity than that of the natural hirudin HV1. The N-terminal region of a hirudin is thought to form an intermolecular bond with the enzyme active center or its adjacent region in the thrombin polypeptide chain. This region is also thought to control the dissociation rate of the hirudin-thrombin complex.

In contrast to the idea of making hirudin analogs by introducing artificial point mutations to the natural type hirudins as mentioned above, the present inventors have produced hybrid hirudins such as HV1C3 by substituting the C-terminal region polypeptide of the HV1 with an C-terminal region polypeptide of the HV3. Among these, the present inventors have demonstrated that this hybrid type hirudin HV1C3 shows a higher antithrombin activity than that of the hirudin HV1 preferably insert EP-A-511393 (Japanese laid-open patent publication 4-173798). Furthermore, such hirudins exhibiting high antithrombin activities were shown to have pharmacological efficacy as antithrombotics which suppress the coagulation process caused by the digestion of polypeptide chains by thrombin. In other words, it has been clearly demonstrated that the coagulation inhibition or suppression properties of the compounds were due to their antithrombin activity.

The present inventors have prepared anticoagulants with the above-mentioned hybrid hirudin analogs such as HV1C3, which was proposed in our previous patent application, as active ingredients in such a manner so that one pure hirudin analog is contained in a certain pharmacological equivalent amount. When these formulations were stored at room temperature for an extended period, changes in the apparent pharmacological activities were observed. The present inventors have investigated the causes of these changes and have discovered the fact that, in the case of HV1C3, a succinimide form and a β form of the Asp$^{33}$-Gly$^{34}$ were formed between the carboxyl residue of the Asp$^{33}$ and its C-terminal adjacent to Gly$^{34}$ (Japanese Laid-Open Patent Publication No. 5-310788). This succinimide form and β form exhibit antithrombin activities like the original hirudin, but the activities are lower, which lead to a decrease in the apparent antithrombotic activities. Furthermore, based on a report that a succinimide form or a β form can be produced by a chemical reaction between the Asp and the amino acid adjacent to it on the C-terminal side, the present inventors have studied this chemical conversion in more detail and have found a possibility that the succinimide form or β form can also be produced at Asp$^{62}$-Ala63-.

This succinimide form and β form (hereafter "hirudin variants") can be produced during the storage following preparation of a hirudin anticoagulant in an appropriate formulation, and this requires extra considerations to keep the pharmacological activity of the anticoagulant agent above a certain preferred level of activity. These might include a low temperature storage, for example, or an increase in the initial amount of hirudin analogs in the formulation in consideration of loss of the pharmacological activity during room temperature storage. Increasing the initial amount of hirudin analogs in the formulation, however, causes problems by unnecessarily elongating the clearance time of the drug in the blood following administration.

DISCLOSURE OF INVENTION

The present invention was made to solve the problems resulting from the production of succinimide or β form. In other words, the purpose of the present invention is to produce high antithrombin activity hirudin analogs with the property of suppressing the conversion of hirudin analogs to hirudin variants by substituting the amino acid sequence, in which the production of the succinimide or β form is likely to occur, to other amino acid sequences.

Furthermore, the present invention provides novel hirudin analogs exhibiting sufficiently high antithrombin activities to cover the concentration decrease of the hirudin analogs due to their conversion to hirudin variants by the formation of succinimides or β forms.

The purpose of the present invention is to produce novel hirudin analogs which make it possible to avoid increasing the total concentration of hirudin in the anticoagulant formulation. This was achieved by maintaining the loss of pharmacological activity within the allowable range by suppressing the decrease of hirudin analogs which occurs upon their conversion to hirudin variants. This was also done by providing novel hirudin analogs with sufficiently high antithrombin activities to allow the required level of pharmacological activity to be obtained without overly increasing the concentration of hirudin analogs, even if the concentration of the hirudin analogs decreases upon their conversion to hirudin variants.

The present invention relates to novel hirudin analogs with the amino acid sequence shown below (SEQ. ID. 1)

Xaa Xaa Tyr Thr Asp Cys Thr Glu Ser Gly Gln Asn Leu Cys Leu
Cys Glu Gly Ser Asn Val Cys Gly Gln Gly Asn Xaa Cys Ile
Leu Gly Ser Xaa Xaa Xaa Xaa Asn Gln Cys Val Thr Gly Glu
Gly Thr Pro Lys Pro Gln Ser His Asn Gln Gly Asp Phe Glu
Pro Ile Pro Glu Xaa Xaa Xaa Asp Glu [I]   [I]

wherein Xaa at position 1 is Val or Ile; Xaa at position 2 is Val or Ile; Xaa at position 27 is Lys or Glu; Xaa at position 33 is Asp or Asn or Gln; Xaa at position 34 is Ala or Gly; Xaa at position 35 is Glu or Lys; Xaa at position 36 is Lys or Asp; Xaa at position 62 is Asp or Glu; Xaa at position 63 is Ala or Tyr or a bond; and Xaa at position 64 is Tyr or Leu, wherein at least one residue at position 63 or 64 is always Tyr.

The hirudin analogs shown in general formula I above can be roughly classified into two groups according to the amino acid sequence difference from HV1C3, the amino acid sequence of which forms the basis in this formula. Group 1 consists of the hirudin analogs having artificial point mutations in one or both of $Asp^{33}$-$Gly^{34}$- and $Asp^{62}$-$Ala^{63}$-, where Asp is included in either amino acid sequence. Group 2 consists of the hirudin analogs having the primary characteristic of the substitution of $Val^1$-$Val^2$- to $Ile^1$-$Ile^2$- in the N-terminal region of the amino acid sequence of the hirudin analog HV1C3. The novel hirudin analogs involved in the present invention also include compounds which belong to both these groups.

The novel hirudin analogs in the present invention can be obtained by modifying the amino acid sequence of a hirudin analog HV1C3. The hirudin analogs of the present invention have the following characteristics:

The hirudin analogs in group 1 among the above-mentioned novel hirudin analogs, those having an artificial point mutation in one or both of $Asp^{33}$-$Gly^{34}$- and $Asp^{62}$-$Ala^{63}$-, where Asp is included in either amino acid sequence, exhibit the characteristic that their conversion to the hirudin variants, which occurs upon the formation of the succinimide form or the β form, is suppressed.

The compounds in group 2, obtained by the substitution of $Val^1$-$Val^2$- to $Ile^1$-$Ile^2$- in the N-terminal region of the amino acid sequence of the hirudin analog HV1C3, exhibit remarkably high antithrombin activities. The reaction rate of the formation of the complex with thrombin, the rate constant, Kon, in particular, was shown to be remarkably high compared with that of HV1C3. In spite of having the same amino acid sequence in the C-terminal, where the first intermolecular binding is said to occur when hirudins form a complex with thrombins, the complex formation rate was remarkably increased.

Furthermore, the novel hirudin analogs in the present invention preserve the antithrombin activity of the hirudin analog HV1C3 as well as the amino acid sequence which leads to pharmacological activity as an anticoagulant based on antithrombin activity. The clearing process of the compounds in the blood by metabolism is therefore naturally expected to be no different from that of the hirudin analog HV1C3.

In the above-mentioned novel hirudin analogs, the characteristic of the suppression of the conversion to hirudin variants caused by the formation of the succinimide form and the β form and the characteristic of antithrombin activity, particularly the increased reaction rate of complex formation with thrombin, are obtained by modifying the separate and independent amino acid sequence which makes these characteristics independent from each other.

Moreover, the present invention relates to novel DNA, an example of which is shown below, which encodes the amino acid sequence of these hirudin analogs: (SEQ. ID. 2)

GTT GTA TAC ACT GAT TGT ACT GAA TCT GGC CAG AAC
CTG TGT CTG TGT GAA GGA TCC AAC GTT TGT GGT
CAG GGT AAC AAA TGT ATC CTC GGG TCT NNN NNN
NNN AAC CAG TGT GTT ACT GGT GAA GGT ACC CCG
AAA CCG CAG TCT CAT AAC CAG GGT GAT TTC GAA
CCG ATC CCG GAA NNN NNN NNN GAT GAA
CTA CTT                                       [II]

wherein NNN at positions 97–99 are GAT, AAC or CAG; NNN at positions 100–102 are GCT or GGT; NNN at positions 103–105 are GAA or AAA; NNN at positions 106–108 are AAG or GAT; NNN at positions 184–186 are GAC or GAA; NNN at positions 187–189 are GCG, TAC, or a bond; and, NNN at positions 190–192 are TAC or CTG.

Furthermore, the present invention is related to a novel hirudin analog expression vector comprising the promoter, the DNA sequence coding for the signal peptide, the DNA sequence coding for the amino acid sequence of the polypeptide shown in SEQ. ID 1, the DNA sequence containing the transcription termination signal, and the DNA sequence containing the replication origin.

The present invention also concerns novel recombinant E. coli which are transformed by the above-mentioned hirudin analog expression vector.

In addition, the present invention concerns a method of manufacturing novel hirudin analogs by incubating the above-mentioned recombinant E. coli in a medium, and extracting the hirudin analogs shown in SEQ. ID. 1 from the cell and/or the medium.

The hirudin analogs of the present invention shown in the above mentioned SEQ. ID. 1 can be produced either by chemical synthesis or by a genetic engineering method.

To produce them by genetic engineering, as shown in one of the examples in this specification, the hirudin-analog-secreting plasmid pMTSHV1C3 (Japanese laid-open patent: 04-173798) must first be digested by the restriction enzyme to remove the DNA sequence coding for the 31st to 44th amino acids. On the other hand, a DNA sequence coding for the 31st to 44th amino acids of the sequence shown in SEQ. ID. 1 is chemically synthesized. The DNA obtained by removing the DNA sequence coding for the 31st to 44th amino acids from the plasmid pMTSHV1C3 is reacted with the chemically synthesized DNA coding for the 31st to 44th amino acids of the sequence of SEQ. ID. 1 using DNA ligase, etc., to construct a plasmid pCX397DA, pCX397NA, or pCX397N containing DNA coding for the amino acid sequence of the hirudin analogs of the present invention These plasmids are further digested individually by restriction enzymes to remove the DNA sequence coding for 45th to 66th amino acids. DNA sequence coding for the 45th to 66th amino acids of the sequence shown by SEQ. ID. 1 is chemically synthesized in parallel. The DNA obtained by removing the DNA sequence coding for the 45th to 66th amino acids of the hirudin analogs CX397DA, CX397NA, and CX397N from these plasmids pCX397DA, pCX397NA, and pCX397N, respectively, is reacted with the chemically synthesized DNA coding for the 45th to 66th amino acids of the sequence in SEQ. ID. 1 using DNA ligase, etc., to construct plasmids containing DNA coding for the amino acid sequence of the hirudin analogs of the present invention: pCX397DA1, pCX397DA2, pCX397DA3, pCX397NA1, pCX397NA2, pCX397NA3, pCX397N1, pCX397N2, and pCX397N3.

These plasmids contain a promoter derived from the plasmid pMTSHV1C3, a DNA sequence encoding a signal peptide, and transcription termination signal. They integrate the DNA sequence coding for the hirudin analogs of the present invention between the DNA sequence coding for the signal peptide and the transcription termination signal.

E. coli were transformed with these plasmids, and the transformed microorganisms produce the hirudin analogs of the present invention in the microorganisms and medium upon culturing.

The hirudin analogs of the present invention may be produced using generally well-known hosts and vector systems for genetic engineering techniques in addition to those mentioned above. Appropriate microorganism hosts include the above-mentioned *Escherichia coli, Bacillus subtilis*, and *Saccharomyces cerevisiae*, for example, from which hirudin analogs can be produced using an expression vector depending on the host cells.

The hirudin analogs of the present invention are usually isolated using a generally known method and purified by chromatography, reverse phase HPLC, and other purification methods.

The hirudin analogs thus obtained, in which the formation of the succinimide form or β form is suppressed as compared with the hirudin HV1 and the hirudin analog HV1C3 (Japanese laid-open patent: 04-173798), is thus highly stable. They also retain a high level of antithrombin activity.

In order to prepare the anticoagulants of the present invention, generally known methods for the production of pharmaceutical preparations can be applied and excellent anticoagulants can be obtained. This is to say that the hirudin analogs of the present invention can be formulated using any conventional carriers and excipient and any conventional methods. The anticoagulants of the present invention may be administered intravenously, intradermally, subcutaneously as well as intramuscularly, locally or parenterally. Although the dosage is individually determined depending on such factors as the symptoms, age and sex of the patient to whom it is to be administered, 0.1–100 mg/day is generally administered to adults in one or more portions.

The novel hirudin analogs of the present invention classified in group 1—which may be obtained by modification of the amino acid sequence of the hirudin analog HV1C3 or by artificial point mutation of one or both of two Asp-containing partial sequences, the $Asp^{33}$-$Gly^{34}$ region and $Asp^{62}$-$Ala^{63}$ region of the amino acid sequence of the hirudin analog HV1C3—exhibit antithrombin activity comparable to that of the hirudin analog HV1C3 and its conversion to the hirudin variants through the formation of succinimide or β form is suppressed, and thereby anticoagulants containing such analogs have the advantage of suppressed decrease in the pharmacological activities, and those classified in group 2—which may be obtained by substitution of $Val^1$-$Val^2$- to $Ile^1$-$Ile^2$- in the N-terminal region of the amino acid sequence of the hirudin analog HV1C3—exhibit a remarkably high antithrombin activity as compared with the hirudin analog HV1C3, and thereby offer such advantages as allowing the total concentration of the hirudin analog contained in the anticoagulant necessary to satisfy the desired pharmacological activity to be kept at a level which is at least lower than that employing the conventional hirudin analog HV1C3, even when conversion to the hirudin variants through formation of the succinimide form or β form occurs. The anticoagulants of the present invention are therefore useful, since they effectively improve a disadvantage of anticoagulants containing the conventional hirudin analog HV1C3: the need to increase the total amount of the concentration contained in advance in order to compensate for the decrease in pharmacological activity during storage.

Since the said novel hirudin analogs are produced in the manufacturing method of the present invention by genetic engineering techniques such as those used in the case of the conventional hirudin analog HV1C3, they can be produced in a large amount with a high reproducibility and are consequently relatively inexpensive.

BRIEF EXPLANATION OF THE DRAWINGS

FIG. 3 represents the concept of the construction of the hirudin analog CX397NA secreting plasmid pCX397NA.

FIG. 6 represents the DNA sequence of the synthetic DNA coding for a part of a hirudin analog employed in the present invention. Oligonucleotides 1-1, 1-2, 1-3, 1-4, 2-1, 2-2, 2-3, 2-4, 3-1, 3-2, 3-3, and 3-4 correspond to SEQ ID NOs: 10, 12, 14, 15, 16, 18, 20, 21, 22, 24, 26, and 27, respectively.

THE MOST PREFERRED EMBODIMENT OF THE PRESENT INVENTION

The present invention will be further explained by means of specific examples for the purpose of showing by one-to-one comparison the characteristics of the amino acid sequence of the novel hirudin analogs of the present invention, the accompanying characteristic of suppression of conversion to hirudin variants through formation of the succinimide or β form, and the accompanying characteristic of elevation of anti-thrombin activity, especially elevation of the reaction rate of the formation of the complex with thrombin. In the following examples, the above-mentioned effects are clarified by disclosing hirudin analogs representing the two groups characterized by the respective modifications of the amino acid sequence mentioned above.

EXAMPLE 1

Production of Hirudin Analogs and Plasmids Expressing Them

1) Production of the Hirudin Analog CX397DA Expression Plasmid pCX397DA

Figures 1, 7:
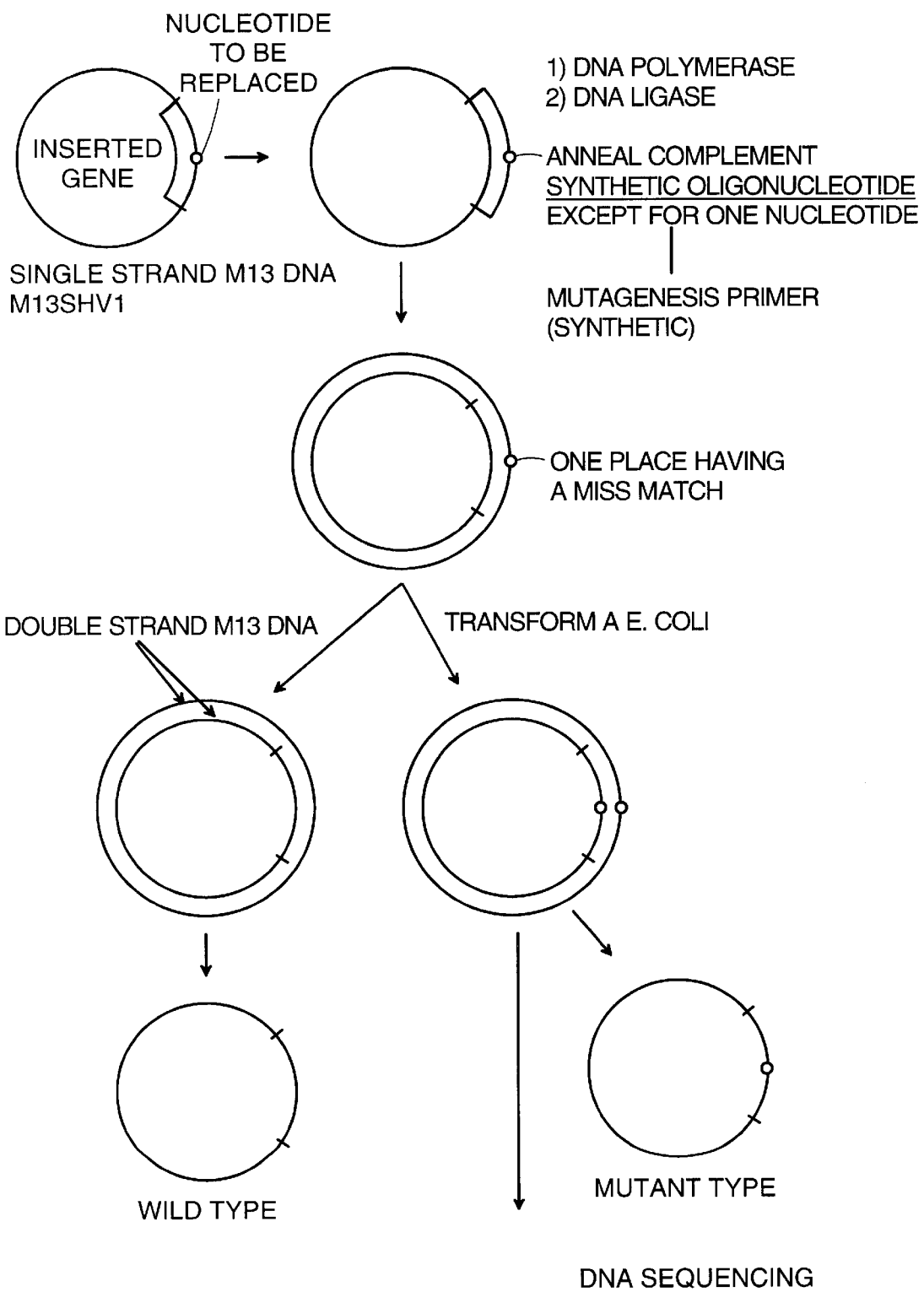
FIG. 1 represents the concept of the construction of the hirudin analog CX397DA secreting plasmid pCX397DA.
FIG. 7 represents the concept of the method of producing a hirudin analog gene, introducing the gene into the secreting expression plasmid pMTSHV19 or pMTSHV10, and transforming the JM109 or RR1 strain by using the plasmid.
Figures 2, 7:
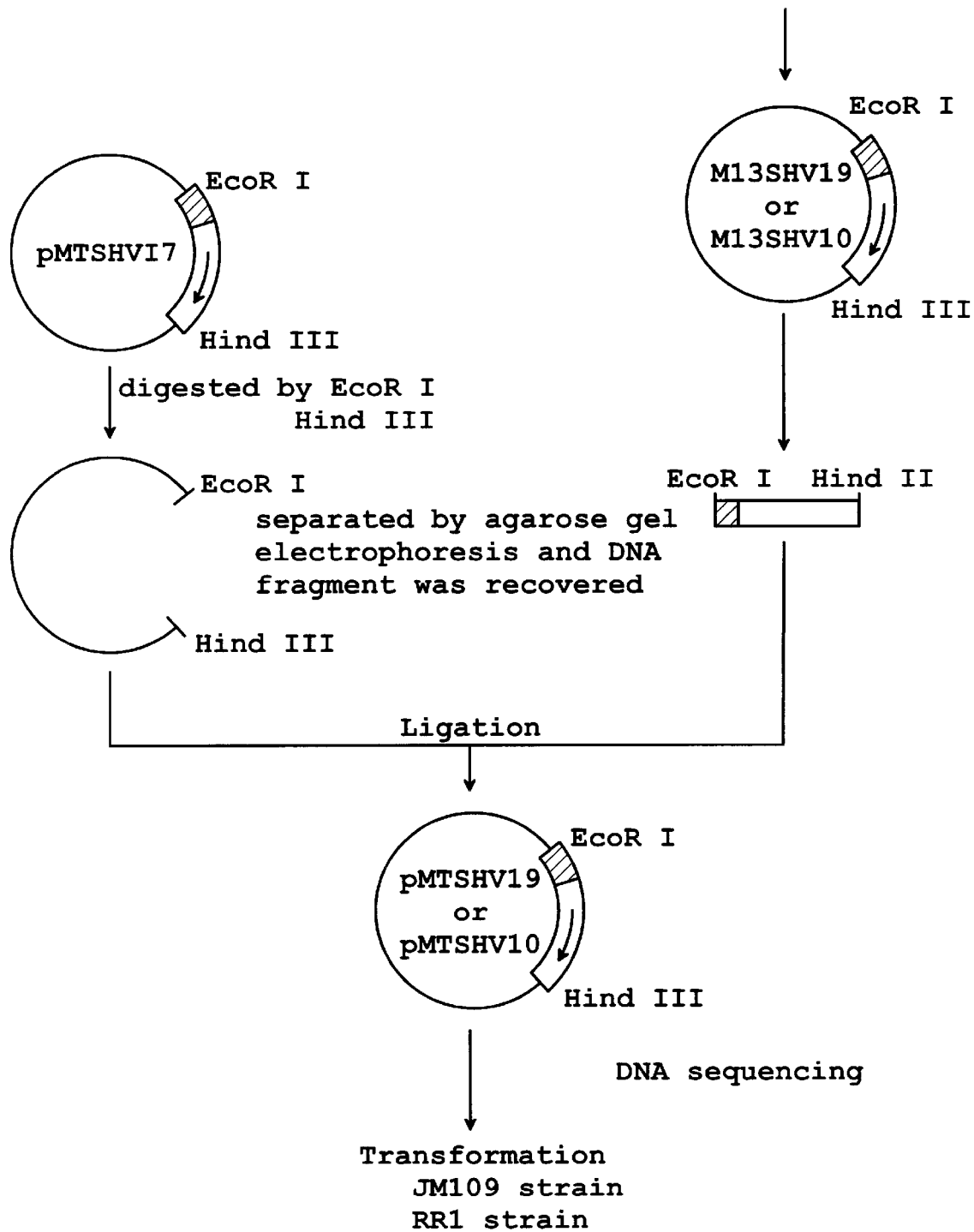
FIG. 2 represents the DNA sequence of the synthetic DNA coding for a part of a hirudin analog employed in the present invention. Oligonucleotides DA-1, DA-2, NA-1, and NA-2 correspond to SEQ ID NOs: 4, 6, 7, and 9, respectively.

The plasmid pCX397DA was constructed according to the method shown in FIG. 1. First, in order to obtain a DNA fragment corresponding to positions 31–44 of the hirudin analog CX397DA, the two oligonucleotides shown in FIG. 2(A) were synthesized by the phosphoramidite method using the Applied Biosystems DNA Synthesizer (Model 380B). Following deprotection, each oligonucleotide was purified by polyacrylamide gel electrophoresis.

Two pmol each of two oligonucleotides, DA-1 and DA-2, SEQ ID NOs: 4 and 6, respectively were mixed and annealed to obtain a double-stranded DNA fragment. This fragment and 50 pmol of the plasmid pMTSHV1C3 digested by restriction enzymes AvaI and KpnI were reacted in 100 µl of solution containing T$_4$DNA ligase at 16° C. for 30 minutes. This reaction mixture (10 µl) was used to transform the E. coli JM109 strain to obtain the hirudin analog CX397DA expression plasmid pCX397DA. The DNA sequence was confirmed by the method of Sanger et al.

The E. coli thus transformed was deposited to Fermentation Research Institute of Agency of Industrial Science and Technology of Ministry of International Trade and Industry (referred to as Fermentation Research Institute hereinafter, currently National Institute of Bio-Science and Human Technology) and assigned an accession number for deposition of Fermentation Research Institute No. 3984 (FERM BP-3984).

2) Preparation of Hirudin Analog CX397NA Expression Plasmid pCX397NA

The plasmid pCX397NA was constructed according to the method shown in FIG. 3. In order to obtain a DNA fragment corresponding to positions 31 to 44 of the hirudin analog CX397NA, the two oligonucleotides shown in FIG. 2(B) were synthesized by the phosphoramidite method using Applied Biosystems DNA Synthesizer (Model 380B). Following deprotection, the individual oligonucleotides were purified by polyacrylamide gel electrophoresis.

Two pmol each of oligonucleotides, NA-1 and NA-2, SEQ ID NOs. 7 and 9, respectively were mixed and annealed to obtain a double-stranded DNA fragment. This fragment and 50 pmol of the plasmid pMTSHV1C3 digested by restriction enzymes AvaI and KpnI were reacted in 100 µl of solution containing T$_4$DNA ligase at 16° C. for 30 minutes. This reaction mixture (10 µl) was used to transform the E. coli JM109 strain to obtain the hirudin analog CX397NA expression plasmid pCX397NA. The DNA sequence was confirmed by the method of Sanger et al.

The E. coli thus transformed was deposited to Fermentation Research Institute and assigned an accession number for deposition of Fermentation Research Institute of No. 3980 (FERM BP-3980).

3) Preparation of Hirudin Analog CX397N Expression Plasmid pCX397N

Figure 4:
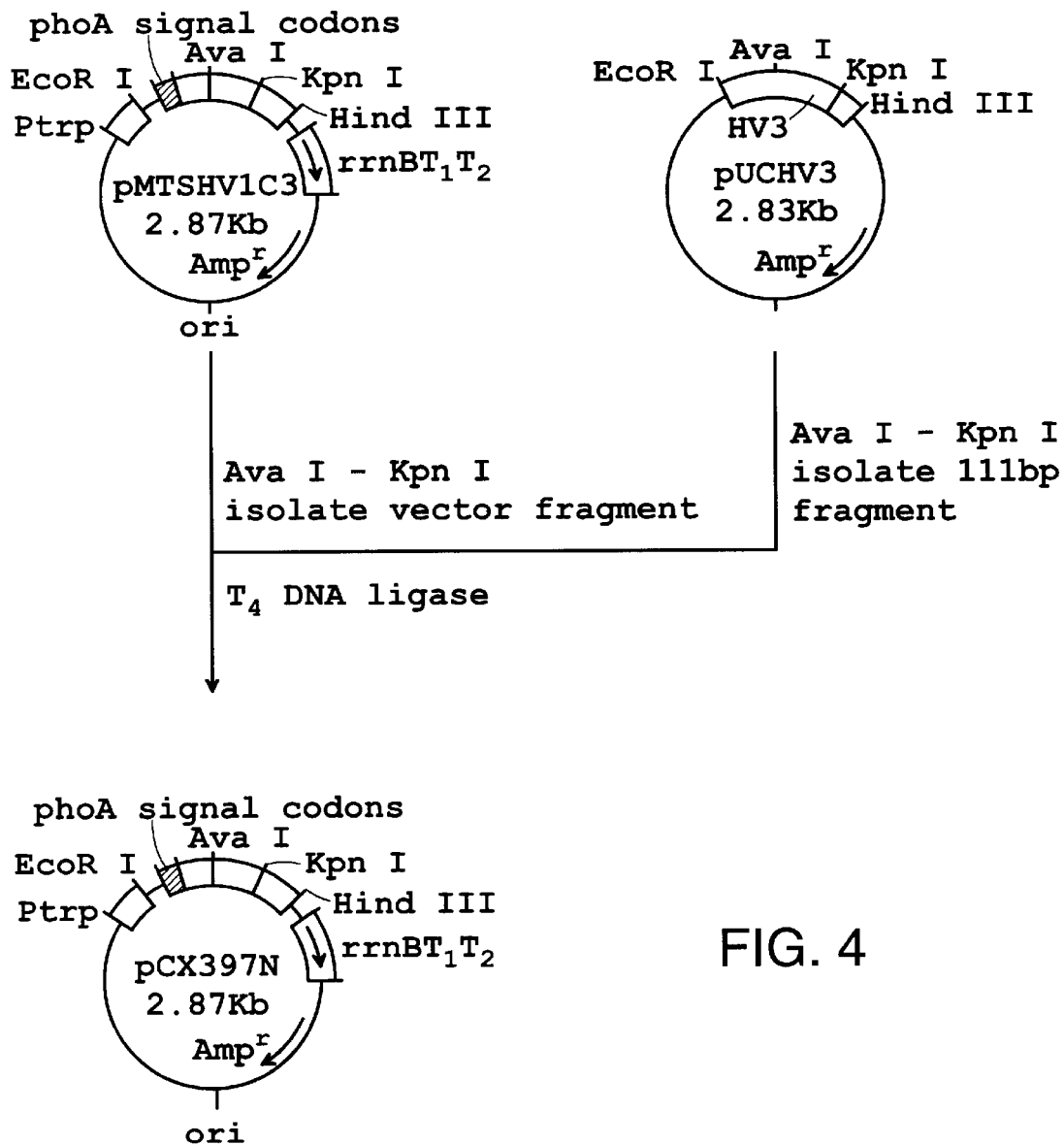
FIG. 4 represents the concept of the construction of the plasmid pCX397N.

The plasmid pCX397N was constructed according to the method shown in FIG. 4. First, the plasmid pUCHV3 (disclosed in a reference example in Japanese laid-open patent publication: 04-173798) was digested by restriction enzymes AvaI and KpnI to obtain a DNA fragment corresponding to positions 31–44 of the hirudin analog CX397N. Ten pmol of this fragment and 50 pmol of the plasmid pMTSHV1C3 (disclosed in the above-mentioned patent publication) digested by restriction enzymes AvaI and KpnI were reacted in 100 µl of solution containing T$_4$DNA ligase at 16° C. for 30 minutes. This reaction mixture (10 µl) was used to transform the E. coli JM109 strain to obtain the hirudin analog CX397N secretion expression plasmid pCX397N. The DNA sequence was confirmed by the method of Sanger et al.

The E. coli thus transformed was deposited to Fermentation Research Institute and assigned an accession number for deposition of Fermentation Research Institute of No. 3976 (FERM BP-3976).

4) Preparation of Hirudin Analog CX397DA1 Expression Plasmid pCX397DA1

Figure 5:
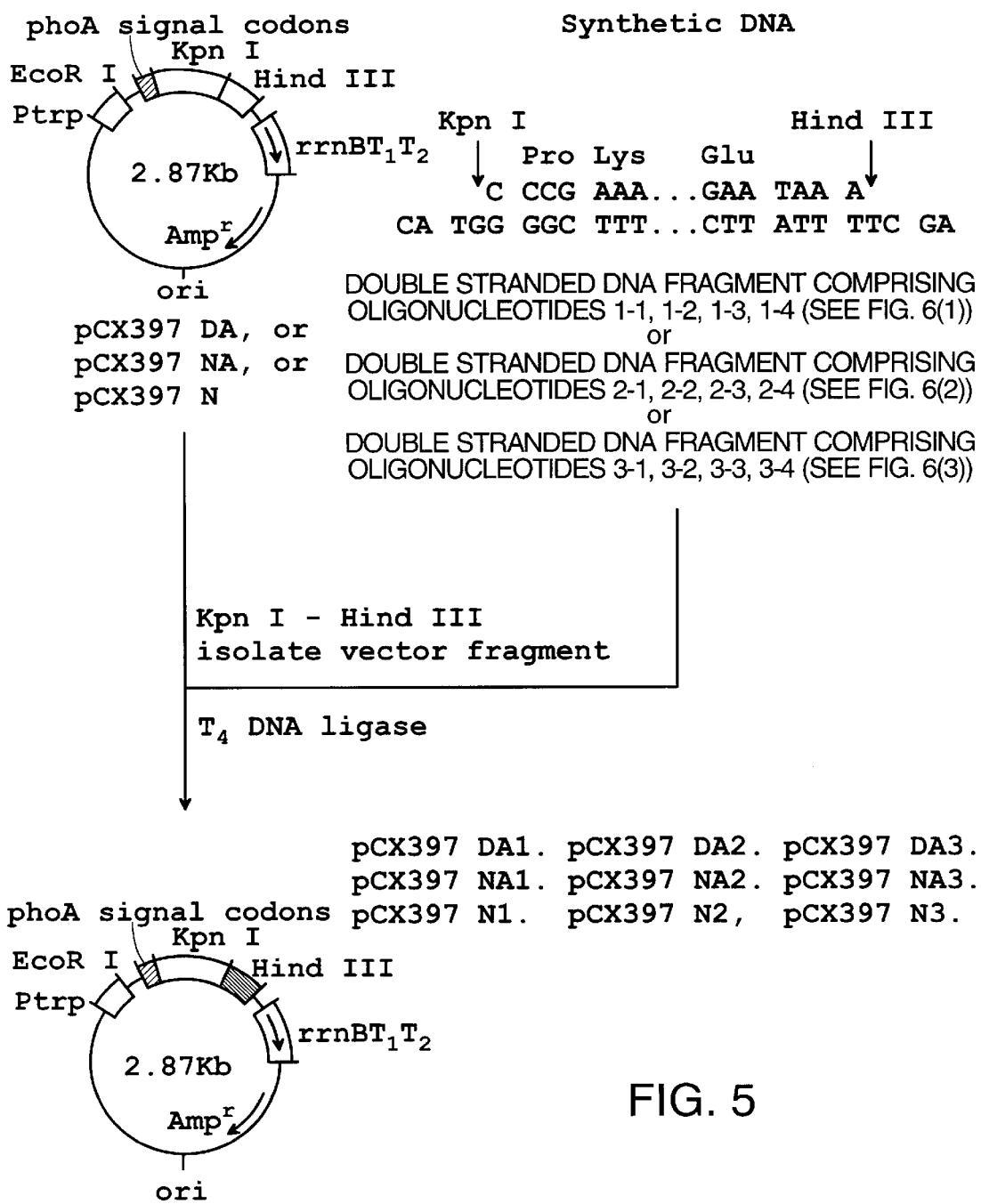
FIG. 5 represents the concept of the construction of the plasmids pCX397DA1, pCX397DA2, pCX397DA3, pCX397NA1, pCX397NA2, pCX397NA3, pCX397N1, pCX397N2, and pCX397N3.

The plasmid pCX397DA1 was constructed according to the method shown in FIG. 5. First, in order to construct a DNA fragment corresponding to the C-terminal region of the hirudin analog CX397DA1, the four oligonucleotides shown in FIG. 6(1) (1-1, 1-2, 1-3, 1-4 SEQ ID NOs. 10, 12, 14 and 15, respectively) were synthesized. Following deprotection, the individual oligonucleotides were purified by polyacrylamide gel electrophoresis.

Following phosphorylation of 50 pmol each of the two oligonucleotides (1-2, 1-3, SEQ ID NOs. 12 and 14, respectively), 2 pmol each of the four oligonucleotides were mixed and annealed to obtain a double-stranded DNA fragment. This fragment and 50 pmol of the plasmid pCX397DA digested by restriction enzymes KpnI and HindIII were reacted in 100 µl of solution containing T$_4$DNA ligase at 16° C. for 30 minutes. This reaction mixture (10 µl) was used to transform the E. coli JM109 strain to obtain the plasmid pCX397DA1. The DNA sequence was confirmed by the method of Sanger et al.

The E. coli thus transformed was deposited to Fermentation Research Institute and assigned an accession number for deposition of Fermentation Research Institute of No. 3985 (FERM BP-3985).

5) Preparation of Hirudin Analog CX397DA2 Expression Plasmid pCX397DA2

The plasmid pCX397DA2 was constructed according to the method shown in FIG. 5. First, in order to construct a DNA fragment corresponding to the C-terminal region of the hirudin analog CX397DA2, the four oligonucleotides shown in FIG. 6(2) were synthesized. Following deprotection, the individual oligonucleotides were purified by polyacrylamide gel electrophoresis.

Following phosphorylation of 50 pmol each of the two oligonucleotides (2-2, 2-3, SEQ ID NOs: 18 and 20, respectively), 2 pmol each of the four oligonucleotides were mixed and annealed to obtain a double-stranded DNA fragment. This fragment and 50 pmol of the plasmid pCX397DA digested by restriction enzymes KpnI and HindIII were reacted in 100 µl of solution containing T$_4$DNA ligase at 16° C. for 30 minutes. This reaction mixture (10 µl) was used to transform the E. coli JM109 strain to obtain the plasmid pCX397DA2. The DNA sequence was confirmed by the method of Sanger et al.

The E. coli thus transformed was deposited to Fermentation Research Institute and assigned an accession number for deposition of Fermentation Research Institute of No. 3986 (FERM BP-3986).

6) Preparation of Hirudin Analog CX397DA3 Expression Plasmid pCX397DA3

The plasmid pCX397DA3 was constructed according to the method shown in FIG. 5. First, in order to construct a DNA fragment corresponding to the C-terminal region of the hirudin analog CX397DA3, the four oligonucleotides shown in FIG. 6(3) were synthesized. Following deprotection, the individual oligonucleotides were purified by polyacrylamide gel electrophoresis.

Following phosphorylation of 50 pmol each of the two oligonucleotides (3-2, 3-3, SEQ ID NOs: 24 and 26, respectively), 2 pmol each of the four oligonucleotides were mixed and annealed to obtain a double-stranded DNA fragment. This fragment and 50 pmol of the plasmid pCX397DA digested by restriction enzymes KpnI and HindIII were reacted in 100 μl of solution containing $T_4$DNA ligase at 16° C. for 30 minutes. This reaction mixture (10 μl) was used to transform the E. coli JM109 strain to obtain the plasmid pCX397DA3. The DNA sequence was confirmed by the method of Sanger et al.

The E. coli thus transformed was deposited to Fermentation Research Institute and assigned an accession number for deposition of Fermentation Research Institute of No. 3987 (FERM BP-3987).

7) Preparation of Hirudin Analog CX397NA1 Expression Plasmid pCX397NA1

The plasmid pCX397NA1 was constructed according to the method shown in FIG. 5. First, in order to construct a DNA fragment corresponding to the C-terminal region of the hirudin analog CX397NA1, the four oligonucleotides shown in FIG. 6(1) were synthesized. Following deprotection, the individual oligonucleotides were purified by polyacrylamide gel electrophoresis.

Following phosphorylation of 50 pmol each of the two oligonucleotides (1-2, 1-3, SEQ ID NOs: 12 and 14, respectively), 2 pmol each of the four oligonucleotides were mixed and annealed to obtain a double-stranded DNA fragment. This fragment and 50 pmol of the plasmid PCX397NA digested by restriction enzymes KpnI and HindIII were reacted in 100 μl solution containing $T_4$DNA ligase at 16° C. for 30 minutes. This reaction mixture (10 μl) was used to transform the E. coli JM109 strain to obtain the plasmid pCX397NA1. The DNA sequence was confirmed by the method of Sanger et al.

The E. coli thus transformed was deposited to Fermentation Research Institute and assigned an accession number for deposition of Fermentation Research Institute of No. 3981 (FERM BP-3981).

8) Preparation of Hirudin Analog CX397NA2 Expression Plasmid pCX397NA2

The plasmid pCX397NA2 was constructed according to the method shown in FIG. 5. First, in order to construct a DNA fragment corresponding to the C-terminal region of the hirudin analog CX397NA2, the four oligonucleotides shown in FIG. 6(2) were synthesized. Following deprotection, the individual oligonucleotides were purified by polyacrylamide gel electrophoresis.

Following phosphorylation of 50 pmol each of the two oligonucleotides (2-2, 2-3, SEQ ID NOs: 18 and 20, respectively), 2 pmol each of the four oligonucleotides were mixed and annealed to obtain a double-stranded DNA fragment. This fragment and 50 pmol of the plasmid pCX397NA digested by restriction enzymes KpnI and HindIII were reacted in 100 μl of solution containing $T_4$DNA ligase at 16° C. for 30 minutes. This reaction mixture (10 μl) was used to transform the E. coli JM109 strain to obtain the plasmid pCX397NA2. The DNA sequence was confirmed by the method of Sanger et al.

The E. coli thus transformed was deposited to Fermentation Research Institute and assigned an accession number for deposition of the Fermentation Research Institute of No. 3982 (FERM BP-3982).

9) Preparation of Hirudin Analog CX397NA3 Expression Plasmid pCX397NA3

The plasmid pCX397NA3 was constructed according to the method shown in FIG. 5. First, in order to construct a DNA fragment corresponding to the C-terminal region of the hirudin analog CX397NA3, the four oligonucleotides shown in FIG. 6(3) were synthesized. Following deprotection, the individual oligonucleotides were purified by polyacrylamide gel electrophoresis.

Following phosphorylation of 50 pmol each of the two oligonucleotides (3-2, 3-3, SEQ ID NOs: 24 and 26, respectively), 2 pmol each of the four oligonucleotides were mixed and annealed to obtain a double-stranded DNA fragment. This fragment and 50 pmol of the plasmid pCX397NA digested by restriction enzymes KpnI and HindIII were reacted in 100 μl of solution containing $T_4$DNA ligase at 16° C. for 30 minutes. This reaction mixture (10 μl) was used to transform the E. coli JM109 strain to obtain the plasmid pCX397NA3. The DNA sequence was confirmed by the method of Sanger et al.

The E. coli thus transformed was deposited to Fermentation Research Institute and assigned an accession number for deposition of Fermentation Research Institute of No. 3983 (FERM BP-3983).

10) Preparation of Hirudin Analog CX397N1 Expression Plasmid pCX397N1

The plasmid pCX397N1 was constructed according to the method shown in FIG. 5. First, in order to construct a DNA fragment corresponding to the C-terminal region of the hirudin analog CX397N1, the four oligonucleotides shown in FIG. 6(1) were synthesized. Following deprotection, the individual oligonucleotides were purified by polyacrylamide gel electrophoresis.

Following phosphorylation of 50 pmol each of the two oligonucleotides (1-2, 1-3, SEQ NOs: 12 and 14, respectively), 2 pmol each of the four oligonucleotides were mixed and annealed to obtain a double-stranded DNA fragment. This fragment and 50 pmol of the plasmid pCX397N digested by restriction enzymes KpnI and HindIII were reacted in 100 μl of solution containing $T_4$DNA ligase at 16° C. for 30 minutes. This reaction mixture (10 μl) was used to transform the E. coli JM109 strain to obtain the plasmid pCX397N1. The DNA sequence was confirmed by the method of Sanger et al.

The E. coli thus transformed was deposited to Fermentation Research Institute and assigned an accession number for deposition of the Fermentation Research Institute of No. 3977 (FERM BP-3977).

11) Preparation of Hirudin Analog CX397N2 Expression Plasmid pCX397N2

The plasmid pCX397N2 was constructed according to the method shown in FIG. 5. First, in order to construct a DNA fragment corresponding to the C-terminal region of the hirudin analog, the four oligonucleotides shown in FIG. (6) were synthesized. Following deprotection, the individual oligonucleotides were purified by polyacrylamide gel electrophoresis.

Following phosphorylation of 50 pmol each of the two oligonucleotides (2-2, 2-3, SEQ NOs: 18 and 20, respectively), 2 pmol each of the four oligonucleotides were mixed and annealed to obtain a double-stranded DNA fragment. This fragment and 50 pmol of the plasmid pCX397N digested by restriction enzymes KpnI and HindIII were reacted in 100 μl of solution containing $T_4$DNA ligase at 16° C. for 30 minutes. This reaction mixture (10 μl) was used to transform the E. coli JM109 strain to obtain the plasmid pCX397N2. The DNA sequence was confirmed by the method of Sanger et al.

The *E. coli* thus transformed was deposited to Fermentation Research Institute and assigned an accession number for deposit of Fermentation Research Institute of No. 3978 (FERM BP-3978).

12) Preparation of Hirudin Analog CX397N3 Expression Plasmid pCX397N3

The plasmid pCX397N3 was constructed according to the method shown in FIG. 5. First, in order to construct a DNA fragment corresponding to the C-terminal region of the hirudin analog CX397N3, the four oligonucleotides shown in FIG. 6(3) were synthesized. Following deprotection, the individual oligonucleotides were purified by polyacrylamide gel electrophoresis.

Following phosphorylation of 50 pmol each of the two oligonucleotides (3-2, 3-3, SEQ ID NOs: 24 and 26, respectively), 2 pmol each of the four oligonucleotides were mixed and annealed to obtain a double-stranded DNA fragment. This fragment and 50 pmol of the plasmid pCX397N digested by restriction enzymes KpnI and HindIII were reacted in 100 μl of solution containing $T_4$DNA ligase at 16° C. for 30 minutes. This reaction mixture (10 μl) was used to transform the *E. coli* JM109 strain to obtain the plasmid pCX397N3. The DNA sequence was confirmed by the method of Sanger et al.

The *E. coli* thus transformed was deposited to Fermentation Research Institute and assigned an accession number for deposit of Fermentation Research Institute of No. 3979 (FERM BP-3979).

EXAMPLE 2
Production of Hirudin Analogs

The *E. coli* JM109 strains (the *E. coli* strains shown in Example 1, (1)–(12)) which had been transformed by hirudin analog expression plasmids were grown individually in 100 ml of 2×TY medium (Bacto-trypton 16 g/l, Bacto-Yeast Extract 10 g/l, NaCl 5 g/l) containing 100 μg/ml of ampicillin. Following shaking culture at 37° C. for 24 hours, the bacteria were harvested. Each sample (100 ml) of precipitated cells was suspended in 25% sucrose, 50 mM Tris-HCl (pH 7.5), and 1 mM EDTA and treated at room temperature for 10 minutes. The cells were collected by centrifugation at 10,000×g for 10 minutes and then suspended in 100 ml of cold water and subjected to osmotic shock to release the substances contained in the periplasm of the cells. After the cells were removed by centrifugation at 10,000×g for 10 minutes, the periplasm fraction was filtered through a 0.22 μm filter.

$(NH_4)_2SO_4$ (12.9 g) was dissolved in 20 ml of the periplasm fraction obtained as described above, then treated at 4° C. overnight. Following centrifugation at 20,000×g for 30 minutes, the sediment was dissolved in 2 ml of water, which was then filtered through an 0.22 μm filter to obtain a crude hirudin analog sample.

This was analyzed by reverse phase high-performance liquid chromatography under the conditions described below:

Column: YMC-Pack PROTEIN-RP 250×4.6 mm
Solvent A: 0.065% $TFA/H_2O$ B: 0.065% TFA/acetonitrile
Gradient: 17% B/10 min 17→32% B/30 min
Flow rate: 1 ml/min
Detection: 215 nm

EXAMPLE 3
Determination of the Succinimide and β Forms in Hirudin Analogs and Their Decrease in the Storage Test After the crude sample of the hirudin analog obtained in Example 2 and the hirudin analog HV1C3 (control) were stored at 25° C. for four weeks, they were analyzed by reverse phase high-performance liquid chromatography, and the results were compared with those obtained prior to storage.

The succinimide form and β form contained were estimated from the results of the reverse phase chromatography as described below. The peaks which were detected within four minutes before and following the peak elution time of a hirudin analog were considered to be those of the succinimide or β form, and the ratio of the succinimide or β form peak area to the combined succinimide or β form and hirudin analog peak area was determined to be the succinimide or β form content. In other words, the calculation was carried out according to the following formula: (Content of succinimide or β form (%))=(Peak area detected within four minutes before and after the main peak)/[(Main peak area)+(Peak area detected within four minute before and after the main peak)]×100.

The results are as shown in Table 1.

TABLE 1

Succinimide or β Form Content Following Storage of Hirudin Analogs of Group 1 at 25° C. (%)

| E. coli Vector of Example 1 (subsection) | Hirudin Analog Expressed | Amino Acid Sequence for SEQ. ID. 1 at the Following Positions: | | | | | | | Succinimide or β Form Content (%) | | |
|---|---|---|---|---|---|---|---|---|---|---|---|
| | | $Xaa^{33}$ | $Xaa^{34}$ | $Xaa^{35}$ | $Xaa^{36}$ | $Xaa^{62}$ | $Xaa^{63}$ | $Xaa^{64}$ | Prior to Storage | After Storage | Increment |
| pMTSHV1C3 | HV1C3 | Asp | Gly | Glu | Lys | Asp | Ala | Tyr | 3.3 | 17.2 | 13.9 |
| (3) pCX397N | CX397N | Gln | Gly | Lys | Asp | Asp | Ala | Tyr | 0 | 6.6 | 6.6 |
| (10) pCX397N1 | CX397N1 | Gln | Gly | Lys | Asp | Glu | Ala | Tyr | 0 | 2.5 | 2.5 |
| (11) pCX397N2 | CX397N2 | Gln | Gly | Lys | Asp | Asp | bond | Tyr | 0 | 1.1 | 1.1 |
| (12) pCX397N3 | CX397N3 | Gln | Gly | Lys | Asp | Asp | Tyr | Leu | 2.5 | 4.3 | 1.8 |
| (1) pCX397DA | CX397DA | Asp | Ala | Glu | Lys | Asp | Ala | Tyr | 1.0 | 10.2 | 9.2 |
| (4) pCX397DA1 | CX397DA1 | Asp | Ala | Glu | Lys | Glu | Ala | Tyr | 0.2 | 2.4 | 2.2 |
| (5) pCX397DA2 | CX397DA2 | Asp | Ala | Glu | Lys | Asp | bond | Tyr | 1.8 | 1.4 | −0.4 |
| (6) pCX397DA3 | CX397DA3 | Asp | Ala | Glu | Lys | Asp | Tyr | Leu | 1.3 | 4.9 | 3.6 |
| (2) pCX397NA | CX397NA | Asn | Ala | Glu | Lys | Asp | Ala | Tyr | 0.9 | 8.5 | 7.6 |
| (7) pCX397NA1 | CX397NA1 | Asn | Ala | Glu | Lys | Glu | Ala | Tyr | 0 | 3.1 | 3.1 |
| (8) pCX397NA2 | CX397NA2 | Asn | Ala | Glu | Lys | Asp | bond | Tyr | 0 | 1.4 | 1.4 |
| (9) pCX397NA3 | CX397NA3 | Asn | Ala | Glu | Lys | Asp | Tyr | Leu | 0.9 | 5.2 | 4.3 |

The results indicate that the hirudin analogs of the present invention can significantly reduce the formation of succinimide and β forms as compared with the conventional hirudin analog HV1C3, even after storage at 25° C., and that the efficacy is therefore stable.

EXAMPLE 4

Hirudin Analog Purification

Hirudin analog was purified according to the method described below.

The *E. coli* JM109 strains which had been transformed by the hirudin analog expression plasmids were individually subjected to shaking culture in 500 ml of 2×TY medium (Bacto-Trypton 16 g/l, Bacto- Yeast Extract 10 g/l, NaCl 5 g/l) containing 50 μg/ml of ampicillin at 37° C. for 24 hours.

Fifty ml of each sample of precipitated cells was then suspended in 25% sucrose, 50 mM Tris-HCl (pH 7.5), and 1 mM EDTA, and treated at room temperature for 10 minutes. The cells were collected by centrifugation at 10,000×g for 10 minutes, then suspended in 50 ml of cold water and subjected to osmotic shock (4° C. for 30 min.) to release the substances contained in the periplasm of the cells. After the cells were removed by centrifugation at 15,000×g for 15 minutes, the periplasm fraction was filtered through a 0.22 μm filter.

The periplasm fraction thus obtained was separated and eluted by reverse phase high-performance liquid chromatography under the following conditions to collect the hirudin peaks:

Equipment: Waters Co., Ltd.

Column: YMC, PROTEIN-RP, 3.0×25 cm

Solvent A: 0.06% TFA/H20 B: 0.06% TFA/acetonitrile

Gradient: 17% B/5 min 17→32% B/45 min

Flow rate: 15 ml/min

Detection: 215 nm

EXAMPLE 5

1) Antithrombin Activity: Determination of Specific Activity by Chromogenic Assay Specific activity was determined by calorimetric quantification of the rate of inhibition of the synthetic substrate, Chromozyme TH (tosylglycilprolylarginine 4-nitroanilide acetate, Boehringer Mannheim), by the hydrolytic activity of thrombin.

In the case of a reaction volume of 1 ml, a 0.5 unit of human thrombin was added to a buffer solution consisting of 100 mM Tris-HCl (pH 8.5), 150 mM NaCl, and 0.1% polyethyleneglycol 6000. A hirudin analog sample was added, and the mixture was pre-incubated at 37° C. for three minutes. Chromozyme TH was added at a final concentration of 200 μM, and the release of p-nitroanilide, the decomposition product of Chromozyme by thrombin, was determined at a wavelength of 405 nm to obtain the increment of absorption per minute.

The amount of the hirudin analog added was varied, and the absorption increment rate was determined at various hirudin analog concentrations to create a graph with the hirudin analog concentration on its horizontal axis and the absorption increment per minute on its vertical axis. Extrapolation of the graph provided the minimum concentration required to inhibit the hydrolytic activity of thrombin completely, which was set at 0.5 ATU (antithrombin unit).

The specific activities (ATU/mg) of the hirudin analogs of the present invention are shown in Table 2.

(2) Antithrombin Activity: Determination of Inhibition Constant Using Fluorescent Synthetic Substrate A Fluorescent synthetic substrate of thrombin, Boc-Asp (OBzl)-Pro-Arg-MCA(Peptide Institute), and human thrombin were employed to determine the antithrombin activity of various hirudin analogs by the method described below using an inhibition rate in the formation of a complex of the synthetic substrate and thrombin as an index.

To 1,970 μl of buffer solution consisting of 0.05 M Tris-HCl buffer (pH 7.8), 0.1% polyethyleneglycol (M6000), 0.1 M NaCl, and 250 μg/ml human serum albumin (HSA) and preheated to 37° C. were added 10 μl of a solution of the hirudin analog to be tested in the above-mentioned buffer (final concentration: 100 pM) and 10 μl of a solution of synthetic substrate in DMSO (final concentration: 50 pM). The solution in which the hirudin and synthetic substrate were dissolved was pre-incubated at 37° C. for three minutes, after which 10 μl of human thrombin solution (final concentration: 40 pM) was added and the solution was vigorously vortexed to prepare a reaction solution. A reaction to form a complex comprising the synthetic substrate and thrombin began at the time when the human thrombin solution was added and vortexed ($t_0$). The above-mentioned added solutions were adjusted to make respective predetermined concentrations of hirudin concentration $C_{IO}$, synthetic substrate concentration $C_{SO}$, and human thrombin concentration $C_{EO}$ in the reaction solution at the time $t_0$. At the times t following the time $t_0$, when said human thrombin solution was added and agitated, the magnitude of fluorescence emitted from the reaction solution at a wavelength of 450 nm was determined while radiating with the reaction solution an excitation light source with a wavelength of 365 nm. The difference between the fluoresceme determined for the reaction solution and that determined for the solution of thrombin and hirudin concentrations of 0 were plotted against the time passing from the time $t_0$, t ($=t-t_0$), in order to obtain a "progress curve." This "progress curve" corresponds to variations in the concentrations of the complex of the synthetic substrate and thrombin, when formation of the complex of the synthetic substrate and thrombin and that of hirudin and thrombin occur competitively. The variations in the concentrations of the complex of the synthetic substrate and thrombin expressed by the "progress curve" were analyzed according to the method of S. R. Stone et al. [see Biochemistry (1986), 25, pp. 2622–2628 or Biochemistry (1979), 18, pp. 2567–2573] in order to obtain an apparent dissociation constant Ki' of the complex of hirudin and thrombin. From the apparent dissociation constant Ki' thus obtained, a dissociation constant Ki was derived using the relation between the apparent constant Ki' and the dissociation constant Ki shown in the following equation (1):

$$Ki' = Ki \times [1 + C_{SO}/Ks] \tag{1}$$

wherein, Ks is a dissociation constant of a complex of the synthetic substrate and thrombin which is equal to the Michael's constant Km of the enzyme reaction between the synthetic substrate and thrombin (for this example: Ks=11.6 μM). Measurement of each sample was done in triplicate.

The dissociation constants Ki (pM) of the complexes of individual hirudin analogs and thrombin are shown in Table 2. Smaller dissociation constants indicate higher antithrombin activity.

TABLE 2

Antithrombin Activity of Hirudin Analogs

| Hirudin Analogs | Specific Activity (ATU/mg) | Dissociation Constant $K_i$ (pM) |
| --- | --- | --- |
| HV1C3 | 10943 | 0.0433 ± 0.0008 |
| CX397N | 13138 | 0.0374 ± 0.0026 |
| CX397N1 | 11853 | 0.0459 ± 0.0019 |
| CX397N2 | 11133 | 0.107 ± 0.004 |
| CX397N3 | 15164 | 0.101 ± 0.008 |
| CX397DA | 11493 | 0.0355 ± 0.0026 |
| CX397DA1 | 11572 | 0.0510 ± 0.0046 |
| CX397DA2 | 11472 | 0.109 ± 0.006 |
| CX397DA3 | 11565 | 0.106 ± 0.011 |
| CX397NA | 11225 | 0.0360 ± 0.0009 |
| CX397NA1 | 10553 | 0.0457 ± 0.0027 |
| CX397NA2 | 12146 | 0.118 ± 0.004 |
| CX397NA3 | 13713 | 0.113 ± 0.005 |

This table shows that the hirudin analogs of the present invention exhibit almost comparable, or even higher, antithrombin activity than the hirudin analog HV1C3 (which has high antithrombin activity) which the present applicant previously proposed.

EXAMPLE 6

Substitution of Val1- Val2 of HirudinHV1to Ile1-Ile2 by using a single chaim M13SHV1.

1) Mutagen Primer 1: (For $Ile^1$-$Ile^2$ Substitution)

5' ACC AAA GCT ATC ATC TAC ACT GAT 3' (SEQ ID NO:28)

Mutagen Primer 2: (For $Glu^{27}$ Substitution)

5' CAG GGT AAC GAA TGT ATC CTC 3' (SEQ. ID NO:29)

The mutagen primers 1 and 2 having the DNA sequences shown above were synthesized by the phosphoramidite method using the Applied Biosystems Synthesizer (Model 380 D).

2) Preparation of M13SHV1

(a) Digestion of M13mp19 DNA by Restriction Enzymes EcoRI-HindIII

A purified EcoRI-HindIII fragment (7.2 Kb) of M13mp19 was obtained using the method similar to that disclosed in Japanese Patent Application No.03-63909 (Japanese Laid Open Patent Publication 04-173798).

(b) Digestion of Plasmid PMTSHV1 DNA by Restriction Enzymes EcoRI-HindIII

Approximately 10 µg of the hirudin HV1 expression vector pMTSHV1 (Japanese Patent Application No.02-303096) was digested by 36 units of restriction enzyme EcoRI and 60 units of restriction enzyme HindIII. The DNA fragment of about 250 bp encoding a phoA signal peptide and the hirudin HV1 was separated and purified by agarose gel electrophoresis.

(c) Production of Double-stranded M13SHV1 and Preparation of Single strand M13SHV1

Two µl (0.04 pM) of the EcoRI-HindIII digested M13mp19 and ligated and then used for transduction of the E. coli TG1 strain. A single strand M13SHV1 DNA was prepared from the plaque thus obtained according to the method of J. Messing [Methods in Enzymology, 101, 21–78 (1983)](1 mg/ml TE buffer, pH 8.0). The DNA sequence was confirmed by the method of Sanger et al.

3) Site Specific Mutation

The mutagen primers 1 and 2 were phosphorylated at the 5'-terminal using the method similar to that described in Japanese Patent Application No.03-63909.

The mutated DNA (assigned M13SHV19) was prepared using the M13SHV1 and the 5'-phosphorylated mutagen primer 1 mentioned above. The mutation DNA (assigned M13SHV10) was also prepared using the M13SHV1 and 5'-phosphorylated primer 2. In the preparation method, the Amersham's Kit as described in Japanese Patent Application No.03-63909 was employed. (See FIG. 7.)

4) Production of Hirudin Analog Expression Plasmid (a) Digestion of Plasmid pMTSHV17 DNA by Restriction Enzymes EcoRI-HindIII As shown in FIG. 7(2), the hirudin analog HV17 expression vector pMTSHV17 (Japanese Patent Application No.03-63909) was decomposed by restriction enzymes EcoRI-HindIII, and the vector DNA fragment of about 2.2 Kb was separated and purified by agarose gel electrophoresis.

(b) Digestion of Double-stranded M13SHV19 and M13SHV10 by Restriction Enzymes EcoRI-HindIII Double-stranded M13SHV19 DNA was decomposed by restriction enzymes EcoRI-HindIII, and the DNA fragment of about 250 bp encoding a phoA signal peptide and the hirudin analog HV-1–9 was separated and purified by agarose gel electrophoresis. The purified DNA fragment of about 250 bp encoding a phoA signal peptide and the hirudin analog HV-1–10 was obtained from M13SHV10 DNA by a similar manner.

(c) Ligation to Expression Plasmid 3.5 µl of the decomposed and purified substance obtained in (a) above and the decomposed and purified substance obtained from M13SHV19 were ligated using $T_4$ ligase and then used for transformation of the E. col. JM109 strain to obtain the mutant expression plasmid pMTSHV19.

The mutant expression plasmid pMTSHV10 was obtained using a similar method. The DNA sequences were confirmed by the method of Sanger et al. (See FIG. 7.)

(d) Digestion of Mutant Expression Plasmid by Restriction Enzymes EcoRI-HindIII

Figure 8:
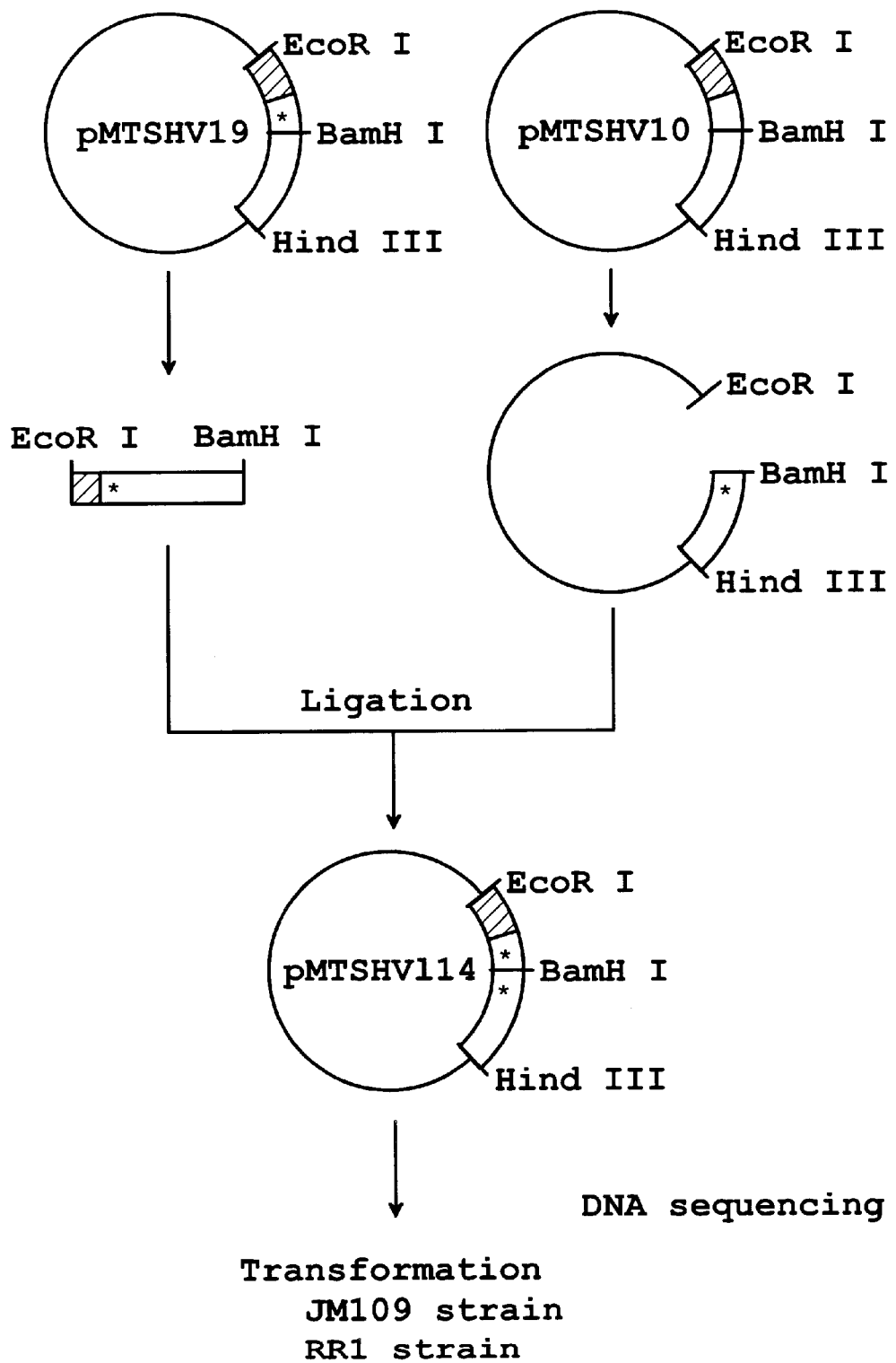
FIG. 8 represents the concept of the construction of a hirudin analog gene with two or more mutations (* indicates hirudin gene.)

About 30 µg of the plasmid pMTSHV19 above was digested by 70 units of restriction enzyme EcoRI and 70 units of BamHI. The DNA fragment of about 120 bp encoding a phoA signal peptide and the N-terminal region of the hirudin analog HV-1–9 was separated and purified by agarose gel electrophoresis. Similarly, the purified EcoRI-BamHI fragment of about 2.7 Kb containing the C-terminal region of the hirudin analog HV-1–10 was obtained using about 30 µg of the plasmid pMTSHV10. (See FIG. 8.)

(e) Preparation of Hirudin Analog Expression Plasmid pMTSHV15

The DNA fragments obtained in (d) above were ligated using $T_4$ ligase and used for transformation of the E. coli JM109 strain to obtain the hirudin analog expression plasmid pMTSHV114. The DNA sequence was confirmed by the method of Sanger et al.

About 17 µg of the plasmid pMTSHV114 was digested by restriction enzymes, 96 units of HindIII and 96 units of KpnI. The fragment containing the DNA sequence encoding a phoA signal peptide and the N-terminal region of the hirudin HV-1–14 was separated and purified by agarose gel electrophoresis.

On the other hand, about 13 µg of the plasmid pUCHV3 (Japanese Patent Application No.02-303098) was digested by 84 units of HindIII and 84 units of KpnI, and the DNA fragment containing the DNA sequence encoding the C-terminal region of the hirudin HV-3, promoter, and transcription termination signal was separated and purified by agarose gel electrophoresis.

Figure 9:
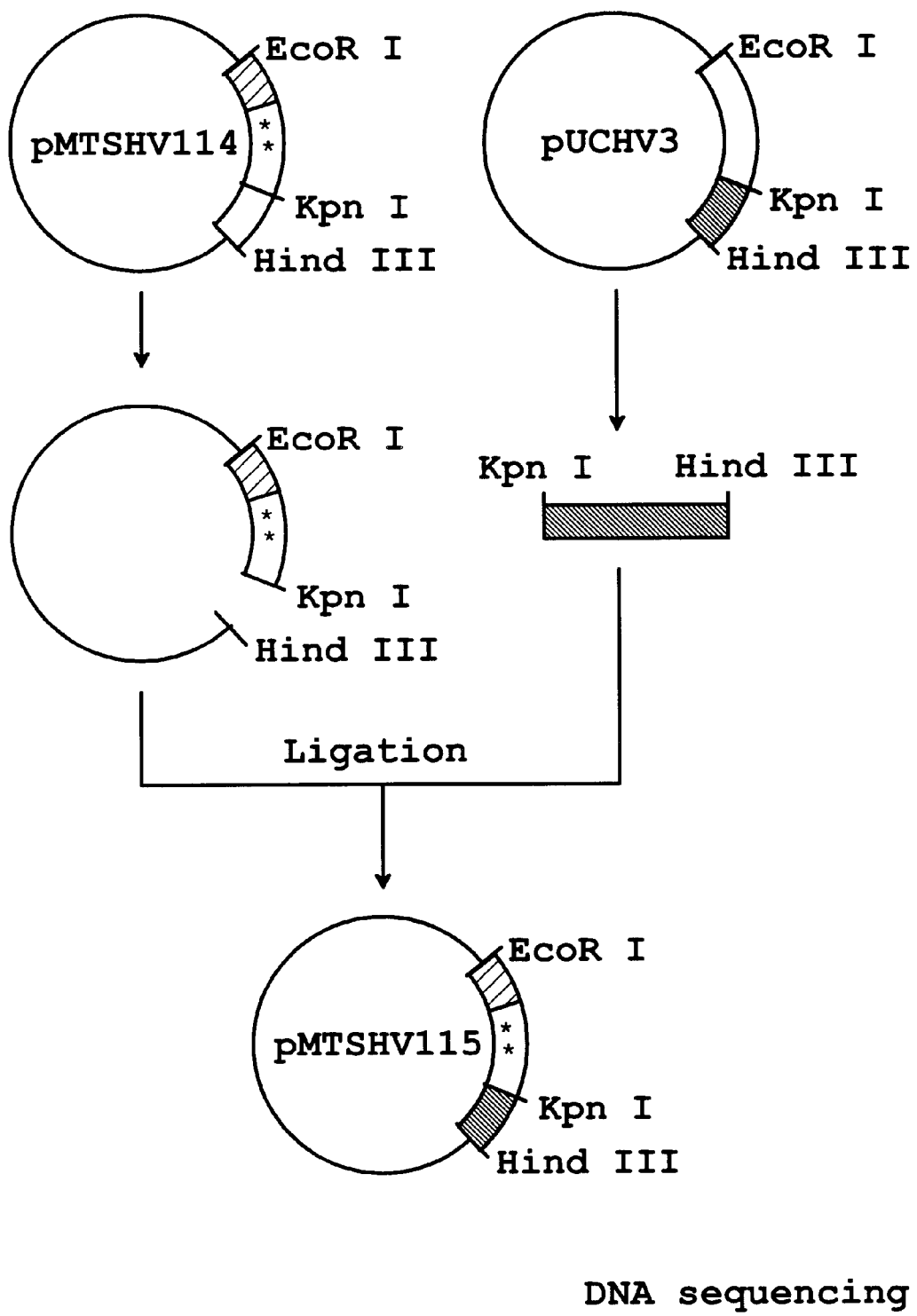
FIG. 9 represents the concept of the construction of a hirudin analog HV-1-15 gene.

The DNA fragments thus obtained were ligated using $T_4$ ligase, and then used to transform the E. coli RR1 strain to obtain the hirudin analog expression plasmid pMTSHV115. The DNA sequence was confirmed by the method of Sanger et al. (See FIG. 9.)

The E. coli thus transformed was deposited to the National Institute of Bio-science and Human Technology of the Agency of Industrial Science and Technology of Ministry of International Trade and Industry and assigned an accession number of FERM BP-4413.

4) Isolation and Purification of Hirudin Analog HV-1–15
(a) Culture of Transformed E. coli RR1/pMTSHV115

The transformed RR1/pMTSHV115 obtained as shown above was subjected to shaking culture in two 2-L flasks containing 500 ml of 2×TY medium with 100 μg/ml of ampicillin at 37° C. for 24 hours.

(b) Isolation of Periplasm Fraction by Osmotic Shock

Following the termination of the culture, the cells were collected by centrifugation, suspended in 1 L of 25% sucrose, 30 mM Tris-HCl (pH 7.4), and 1 mM EDTA, and treated at room temperature for 10 minutes. The bacteria obtained by centrifugation were suspended in 1 L of cold water and treated at 4° C. for 30 minutes to release the substances in the periplasm. The cells were removed by centrifugation, and the supernatant thus obtained was filtered through an 0.22 μm filter.

(c) Purification of Hirudin Analog HV-1–15

About 1 L of the periplasm fraction obtained as described in (b) above was concentrated to about 100 ml by ultrafiltration. The concentrated fraction was loaded on the reverse phase HPLC column under the following conditions, eluted, collected separately, and lyophilized to obtain the hirudin analog HV-1–15:

Equipment: Waters, DeltaPrep 3000

Column: Vydac C4 (4.7×30 cm)

Solvent: A. 0.05% Trifluoroacetic acid/water B. Acetonitrile

Gradient: B. 10–60%/50 min

Flow Rate: B. 80 ml/min

EXAMPLE 7
1) Construction of Hirudin Analog HV-1–16 Expression Plasmid

The plasmid pMTSHC19 obtained in Example 5, 3), (c) above and the plasmid pMTSHV1C3 (Japanese Patent Application No.02-303097) were employed to construct the hirudin analog HV-1–16 expression plasmid pMTSHV116.

(a) Digestion of Analog Expression Plasmid by Restriction Enzymes EcoRI-HindIII

About 6 μg of the plasmid pMTSHV19 was digested by 24 units of the restriction enzyme BamHI and 24 units of the restriction enzyme HindIII. The fragment of about 1.75 kb containing the DNA sequence encoding a promoter, a phoA signal, and the N-terminal region of the hirudin analog HV-1–9 thus obtained was separated and purified by agarose gel electrophoresis.

On the other hand, the plasmid pMTSHV1C3 was similarly digested by restriction enzymes BamHI and HindIII. The fragment of about 150 bp containing the DNA sequence encoding the C-terminal region of the hirudin HV-3 was then separated and purified.

(b) Construction of Hirudin Analog Expression Plasmid pMTSHV116

Figure 10:
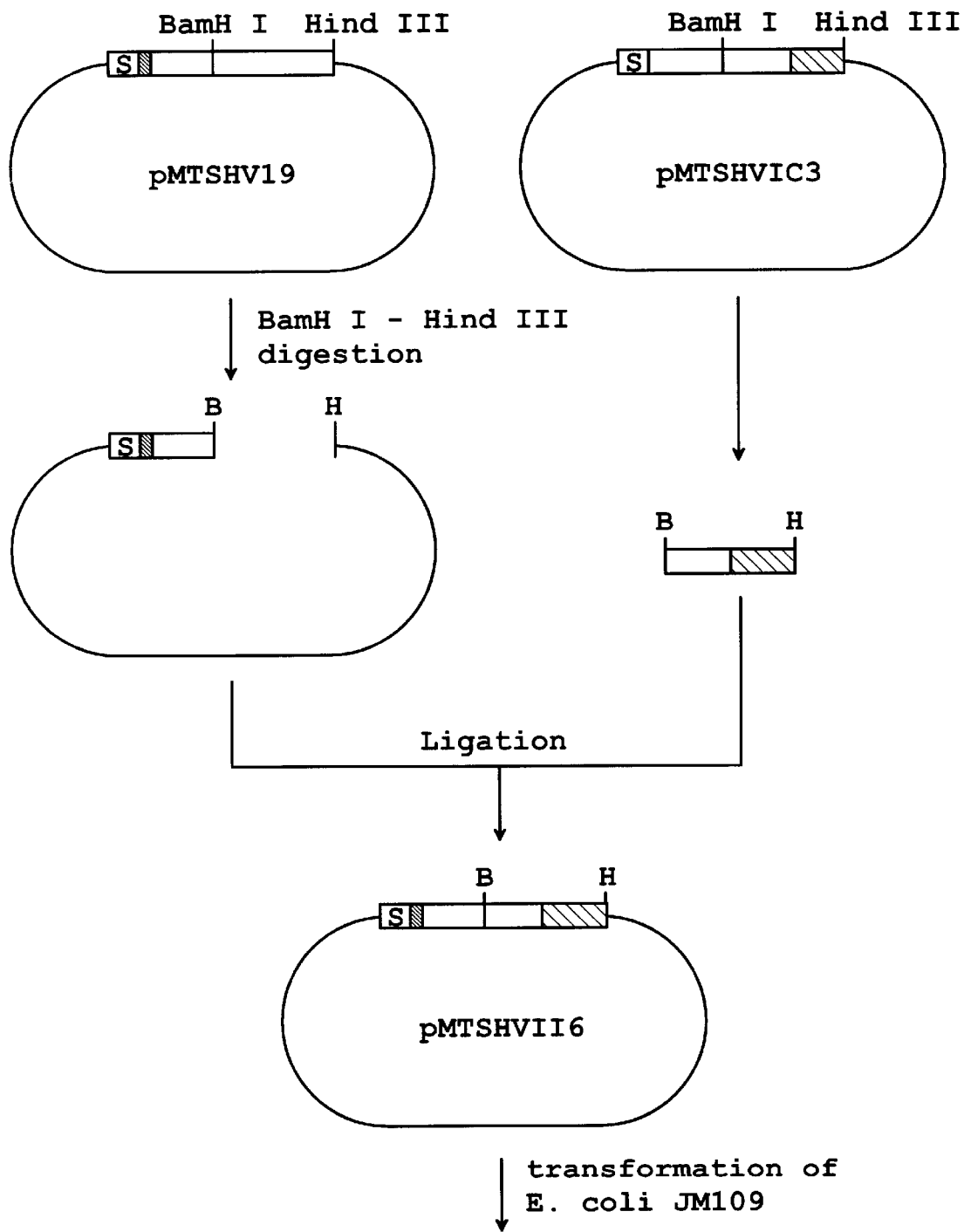
FIG. 10 represents the concept of the construction of a hirudin analog HV-1-16 gene.

The DNA fragments obtained in (a) above were ligated using $T_4$ ligase and then used for transformation of the E. coli JM109 strain to obtain the hirudin analog expression plasmid pMTSHV116. The DNA sequence was confirmed by the method of Sanger et al. (See FIG. 10.)

The E. coli thus transformed was deposited to the National Institute of Bio-science and Human Technology of the Agency of Industrial Science and Technology of Ministry of International Trade and Industry and assigned an accession number of FERM BP-4412.

2) Isolation and Purification of Hirudin Analog HV-1–16

The hirudin analog HV-1–16 was purified using the method similar to that disclosed in Japanese laid-open patent publication 04-282474.

EXAMPLE 8
Determination of Antithrombin Activity of Hirudin Analogs

Antithrombin activity of the hirudin analogs HV-1–15 and HV1–16 was determined according to the method similar to that disclosed in the specification of the Japanese laid-open patent publication 04-282474. The results are shown in Table 3.

Their amino acid compositions are shown in Table 4. In addition to the above-described hirudin analogs HV-1–15 and HV-1–16, the hirudin analog HV-1–9 (wherein $Val^1$-$Val^2$- of the hirudin analog HV-1 was substituted with $Ile^1$-$Ile^2$-) was obtained using the recombinant microorganism, the E. coli JM109 strain transformed by the analog expression plasmid pMTSHV19; the hirudin analog HV-1–10 (wherein $Lys^2$ of the hirudin analog HV-1 was substituted with $Glu^{27}$) using the recombinant microorganism, the E. coli JM109 strain transformed by the analog expression plasmid pMTSHV10; and the hirudin analog HV-1–14 (wherein $Val^1$-$Val^2$- and $Lys^{27}$ of the hirudin analog HV-1 were substituted with $Ile^1$-$Ile^2$- and $Glu^{27}$, respectively) using the recombinant microorganism, the E. coli JM109 strain transformed by the analog expression plasmid pMTSHV114, by culturing the recombinant microorganism, isolating the hirudin analogs from the cultured microorganism and medium, and purifying them.

TABLE 3

Antithrombin Activity of Hirudin Analogs of Group 2

| Hirudins | Amino Acid Sequence for SEQ. ID. 1 at the Following Positions: | | | Ki (pM) | $K_{on} \times 10^{-8}$ ($M^{-1}S^{-1}$) | $K_{off} \times 10^5$ ($S^{-1}$) |
| | $Xaa^1$—$Xaa^2$ | $Xaa^{27}$ | $Gln^{53}$ to C-terminus | | | |
|---|---|---|---|---|---|---|
| rHV-1 | V—V— | —K— | rHV-1 type | 0.148 ± 0.009 | 2.56 ± 0.37 | 3.78 ± 0.51 |
| rHV1C3 | V—V— | —K— | rHV-3 type | 0.0433 ± 0.0008 | 3.33 ± 0.09 | 1.44 ± 0.05 |
| rHV-1-9 | I—I— | —K— | rHV-1 type | 0.0743 ± 0.0044 | 2.58 ± 0.26 | 1.91 ± 0.12 |
| rHV-1-10 | V—V— | —E— | rHV-1 type | 0.237 ± 0.016 | 2.35 ± 0.16 | 5.57 ± 0.16 |
| rHV-1-14 | I—I— | —E— | rHV-1 type | 0.0796 ± 0.0038 | 2.56 ± 0.08 | 2.04 ± 0.16 |
| *rHV-1-15 | I—I— | —E— | rHV-3 type | 0.0226 ± 0.0007 | 4.00 ± 0.44 | 0.907 ± 0.130 |
| *rHV-1-16 | I—I— | —K— | rHV-3 type | 0.0213 ± 0.0006 | 4.58 ± 0.26 | 0.976 ± 0.047 |

TABLE 4

| Amino Acid | HV-1 | HV-1-9 | HV-1-10 | HV-1-14 | HV-1-15 | HV-1-16 |
|---|---|---|---|---|---|---|
| Asx | 9 | 8.86(9) | 8.90(9) | 8.89(9) | 9.93(10) | 9.80(10) |
| Thr | 4 | 3.85(4) | 3.91(4) | 3.88(4) | 3.84(4) | 3.76(4) |
| Ser | 4 | 3.56(4) | 3.66(4) | 3.62(4) | 3.65(4) | 3.52(4) |
| Glx | 13 | 13.46(13) | 14.60(14) | 14.61(14) | 13.78(13) | 12.21(12) |
| Gly | 9 | 9.00(9) | 9.00(9) | 9.00(9) | 9.00(9) | 9.00(9) |
| Cys | 6 | 5.90(6) | 5.91(6) | 5.81(6) | 5.60(6) | 5.09(6) |
| Val | 4 | 1.96(2) | 3.23(4) | 1.96(2) | 1.93(2) | 1.96(2) |
| Ile | 2 | 2.91(4) | 1.96(2) | 2.91(4) | 2.87(4) | 2.72(4) |
| Leu | 4 | 4.14(4) | 4.17(4) | 4.15(4) | 3.07(3) | 2.90(3) |
| Tyr | 2 | 2.07(2) | 2.09(2) | 2.07(2) | 2.04(2) | 1.97(2) |
| Phe | 1 | 1.00(1) | 1.01(1) | 1.01(1) | 0.99(1) | 1.00(1) |
| His | 1 | 1.05(1) | 1.08(1) | 1.03(1) | 1.02(1) | 0.96(1) |
| Lys | 3 | 3.07(3) | 2.05(2) | 2.04(2) | 2.01(2) | 2.97(3) |
| Pro | 3 | 3.12(3) | 3.21(3) | 3.12(3) | 4.06(4) | 4.53(4) |
| Ala | — | — | — | — | 1.09(1) | 1.00(1) |

The values in parenthesis show the composition values. Hydrolysis was performed at 110° C. for 24 hours.
* Equipment Used
Amino Acid Analysis: Amino Acid Analyzer System 7300 (Beckman) N-Terminal Sequence: 477 A Protein Sequencer (Applied Biosystems)

Table 3 shows that the hirudin analogs of the present invention, especially HV-1–15 and HV-1–16, exhibit a higher antithrombin activity than the hirudin analog HV1C3 with high antithrombin activity, especially HV-1–15 and HV-1–16, exhibit a higher antithrombin activity than the hirudin analog HV1C3 (with high antithrombin activity) which the present applicant previously proposed.

EXAMPLE 9

Pharmaceuticals Containing Hirudin Analogs

The purified hirudin analog obtained in Example 4 were desalted by Sephadex G25 (Pharmacia), then filtered aseptically through an 0.22 μm filter. The solution was lyophilized, and the powder thus obtained was dissolved in physiological saline solution to obtain pharmaceuticals which could be used for injection.

The hirudin analogs representing the two groups characterized by modification of the amino acid sequence among the novel hirudin analogs of the present invention and the methods used in their production are explained in the above specific examples. The contents of the above specific examples are sufficient to enable those skilled in the art to prepare a DNA sequence encoding a polypeptide containing an amino acid sequence and to construct an expression vector containing the DNA sequence of the hirudin analogs which belong to either of the two groups, depending on the amino acid sequence, in the light of the production methods described above. In addition, no specific examples are required to show that the hirudin analogs belonging to either of the two groups apparently bear the individual characteristics of the two groups, namely, conversion to the hirudin variants by suppression of the formation of the succinimide or β form as well as antithrombin activity, especially the elevated reaction rate of formation of a complex with thrombin. Moreover, it is also apparent that the physiological mechanism providing the antithrombin activity of the novel hirudin analogs of the present invention is the same as that of the hirudin analog HV1C3, the amino acid sequence of which is quite similar to that of the hirudin analogs of the present invention, and that their pharmacological effects (only the activity shows a slight difference) and metabolic activities are also quite similar.

Industrial Applicability

The present invention provides novel hirudin analogs.

The hirudin analogs of the present invention have a higher antithrombin activity than the conventional hirudin analog HV1C3, suppress decrease in their pharmacological activities due to the formation of succinimide or β form during storage, and are useful as anticoagulants.

Reference of the Deposited Microorganisms

1. *E. coli* JM109/pCX397 N
   Depositary Authority
   Name: Fermentation Research Institute (National Institute of Bioscience and Human-Technology, at the present name) Agency of Industrial Science and Technology Ministry of International Trade and Industry
   Address: 1-3, Higashi 1-chome, Tsukuba-shi, Ibaraki-ken, Japan
   Deposited Date: Aug. 26, HEISEI 4 (1992)
   Accession Number: FERM BP-3976
2. *E. coli* JM109/pCX397 N1
   Depositary Authority
   Name: Fermentation Research Institute (National Institute of Bioscience and Human-Technology, at the present name) Agency of Industrial Science and Technology Ministry of International Trade and Industry
   Address: 1-3, Higashi 1-chome, Tsukuba-shi, Ibaraki-ken, Japan
   Deposited Date: Aug. 26, HEISEI 4 (1992)
   Accession Number: FERM BP-3977
3. *E. coli* JM109/pCX397 N2
   Depositary Authority
   Name: Fermentation Research Institute (National Institute of Bioscience and Human-Technology, at the present name) Agency of Industrial Science and Technology Ministry of International Trade and Industry
   Address: 1-3, Higashi 1-chome, Tsukuba-shi, Ibaraki-ken, Japan
   Deposited Date: Aug. 26, HEISEI 4 (1992)
   Accession Number: FERM BP-3978
4. *E. coli* JM109/pCX397 N3
   Depositary Authority
   Name: Fermentation Research Institute (National Institute of Bioscience and Human-Technology, at the present name) Agency of Industrial Science and Technology Ministry of International Trade and Industry Address: 1-3, Higashi 1-chome, Tsukuba-shi, Ibaraki-ken, Japan
Deposited Date: Aug. 26, HEISEI 4 (1992)
Accession Number: FERM BP-3979

5. *E. coli* JM109/pCX397 NA
Depositary Authority
Name: Fermentation Research Institute (National Institute of Bioscience and Human-Technology, at the present name) Agency of Industrial Science and Technology Ministry of International Trade and Industry
Address: 1-3, Higashi 1-chome, Tsukuba-shi, Ibaraki-ken, Japan
Deposited Date: Aug. 26, HEISEI 4 (1992)
Accession Number: FERM BP-3980

6. *E. coli* JM109/pCX397 NA1
Depositary Authority
Name: Fermentation Research Institute (National Institute of Bioscience and Human-Technology, at the present name) Agency of Industrial Science and Technology Ministry of International Trade and Industry
Address: 1-3, Higashi 1-chome, Tsukuba-shi, Ibaraki-ken, Japan
Deposited Date: Aug. 26, HEISEI 4 (1992)
Accession Number: FERM BP-3981

7. *E. coli* JM109/pCX397 NA2
Depositary Authority
Name: Fermentation Research Institute (National Institute of Bioscience and Human-Technology, at the present name) Agency of Industrial Science and Technology Ministry of International Trade and Industry
Address: 1-3, Higashi 1-chome, Tsukuba-shi, Ibaraki-ken, Japan
Deposited Date: Aug. 26, HEISEI 4 (1992)
Accession Number: FERM BP-3982

8. *E. coli* JM109/pCX397 NA3
Depositary Authority
Name: Fermentation Research Institute (National Institute of Bioscience and Human-Technology, at the present name) Agency of Industrial Science and Technology Ministry of International Trade and Industry
Address: 1-3, Higashi 1-chome, Tsukuba-shi, Ibaraki-ken, Japan
Deposited Date: Aug. 26, HEISEI 4 (1992)
Accession Number: FERM BP-3983

9. *E. coli* JM109/pCX397 DA
Depositary Authority
Name: Fermentation Research Institute (National Institute of Bioscience and Human-Technology, at the present name) Agency of Industrial Science and Technology Ministry of International Trade and Industry
Address: 1-3, Higashi 1-chome, Tsukuba-shi, Ibaraki-ken, Japan
Deposited Date: Aug. 26, HEISEI 4 (1992)
Accession Number: FERM BP-3984

10. *E. coli* JM109/pCX397 DA1
Depositary Authority
Name: Fermentation Research Institute (National Institute of Bioscience and Human-Technology, at the present name) Agency of Industrial Science and Technology Ministry of International Trade and Industry
Address: 1-3, Higashi 1-chome, Tsukuba-shi, Ibaraki-ken, Japan
Deposited Date: August 26, HEISEI 4 (1992)
Accession Number: FERM BP-3985

11. *E. coli* JM109/pCX397 DA2
Depositary Authority
Name: Fermentation Research Institute (National Institute of Bioscience and Human-Technology, at the present name) Agency of Industrial Science and Technology Ministry of International Trade and Industry
Address: 1-3, Higashi 1-chome, Tsukuba-shi, Ibaraki-ken, Japan
Deposited Date: Aug. 26, HEISEI 4 (1992)
Accession Number: FERM BP-3986

12. *E. coli* JM109/pCX397 DA3
Depositary Authority
Name: Fermentation Research Institute (National Institute of Bioscience and Human-Technology, at the present name) Agency of Industrial Science and Technology Ministry of International Trade and Industry
Address: 1-3, Higashi 1-chome, Tsukuba-shi, Ibaraki-ken, Japan
Deposited Date: Aug. 26, HEISEI 4 (1992)
Accession Number: FERM BP-3987

13. *E. coli* JM109/pMTSHV116
Depositary Authority
Name: National Institute of Bioscience and Human-Technology Agency of Industrial Science and Technology Ministry of International Trade and Industry
Address: 1-3, Higashi 1-chome, Tsukuba-shi, Ibaraki-ken, Japan
Deposited Date: Sep. 17, HEISEI 5 (1993)
Accession Number: FERM BP-4412

14. *E. coli* RR1/pMTSHV115
Depositary Authority
Name: National Institute of Bioscience and Human-Technology Agency of Industrial Science and Technology Ministry of International Trade and Industry
Address: 1-3, Higashi 1-chome, Tsukuba-shi, Ibaraki-ken, Japan
Deposited Date: Sep. 17, HEISEI 5 (1993)
Accession Number: FERM BP-4413

We claim:

1. A hirudin analog comprising the amino acid sequence SEQ. ID. 1, wherein $Xaa^1$ is Ile,
$Xaa^2$ is Ile,
$Xaa^{27}$ is Lys or Glu,
$Xaa^{33}$ is Asp or Asn,
$Xaa^{34}$ is Ala,
$Xaa^{35}$ is Glu or Lys,
$Xaa^{36}$ is Lys or Asp,
$Xaa^{62}$ is Asp or Glu,
$Xaa^{63}$ is Ala, Tyr or a peptide bond,
$Xaa^{64}$ is Tyr or Leu, provided that at least one of $Xaa^{63}$ and $Xaa^{64}$ is Tyr.

2. A DNA comprising a nucleotide sequence encoding the hirudin analog of claim 1.

3. A DNA encoding a hirudin analog, said DNA comprising the nucleotide sequence of SEQ. ID. 2, wherein the Ns at positions 97 to 102 are GAT GCT, or AAC GCT,
the Ns at positions 103 to 105 are GAA or AAA,
the Ns at positions 106 to 108 are AAG or GAT,
the Ns at positions 184 to 186 are GAC or GAA,
the Ns at positions 187 to 189 are GCG, TAC or a phosphodiester bond,
the Ns at positions 190 to 192 are TAC or CTG,
provided that at least one set of Ns at positions 187 to 189 or 190 to 192 is TAC.

4. A hirudin analog comprising the amino acid sequence of SEQ. ID. 1, wherein $Xaa^1$ is Ile or Val,
$Xaa^2$ is Ile or Val,
$Xaa^{27}$ is Lys or Glu,
$Xaa^{33}$ is Asp or Asn,
$Xaa^{34}$ is Ala,
$Xaa^{35}$ is Glu or Lys,
$Xaa^{36}$ is Lys or Asp, $Xaa^{62}$-$Xaa^{63}$ are Asp-peptide bond, Asp-Tyr or Glu-Ala, $Xaa^{64}$ is Tyr or Leu, provided that at least one of $Xaa^{63}$ and $Xaa^{64}$ is Tyr.

5. A DNA comprising a nucleotide sequence encoding the hirudin analog of claim 4.

6. A DNA encoding a hirudin analog, said DNA comprising the nucleotide sequence of SEQ. ID. 2, wherein the Ns at positions 97 to 99 are GAT, or AAC, the Ns at positions 100 to 102 are GCT, the Ns at positions 103 to 105 are GAA or AAA, the Ns at positions 106 to 108 are AAG or GAT, the Ns at positions 184 to 189 are GAC phosphodiester bond, GAC TAC or GAA GCG, the Ns at positions 190 to 192 are TAC or CTG, provided that at least one set of Ns at positions 187 to 189 or 190 to 192 is TAC.

7. A hirudin analog comprising the amino acid sequence of SEQ. ID. 1, wherein $Xaa^1$ is Ile or Val, $Xaa^2$ is Ile or Val, $Xaa^{27}$ is Lys or Glu, $Xaa^{33}$-$Xaa^{34}$ are Asp-Ala, or Asn-Ala, $Xaa^{35}$ is Glu or Lys, $Xaa^{36}$ is Lys or Asp, $Xaa^{62}$ is Asp or Glu, $Xaa^{63}$ is Ala, Tyr or a peptide bond, $Xaa^{64}$ is Tyr or Leu, provided that at least one of $Xaa^{63}$ and $Xaa^{64}$ is Tyr.

8. A DNA comprising a nucleotide sequence encoding the hirudin analog of claim 7.

9. A DNA encoding a hiruding analog, said DNA comprising the nucleotide sequence of SEQ. ID. 3, wherein the Ns at positions 79 to 81 are GAA.

10. A hirudin analog expression vector having a nucleotide sequence comprising the DNA of claim 2, 5, or 8.

11. A recombinant microorganism comprising the expression vector of claim 10.

12. A method of manufacture of a hirudin analog comprising the steps of:

culturing the recombinant microorganism of claim 11 under conditions which permit hirudin production; and harvesting the hirudin analog produced by said microorganism.

13. A composition having anticoagulant properties comprising:

the hirudin analog of claim 1, 4 or 7; and a pharmaceutically suitable carrier wherein the hirudin analog is present at a concentration effective for anti-thrombin activity.

14. A hirudin analog comprising the amino acid sequence of SEQ. ID. 1, wherein $Xaa^1$-$Xaa^2$ is Ile-Ile, $Xaa^{27}$ is Glu, $Xaa^{33}$-$Xaa^{34}$ is Gln-Gly, $Xaa^{35}$ is Glu or Lys, $Xaa^{62}$-$Xaa^{63}$ are Asp-peptide bond, Asp-Tyr, or Glu-Ala, and $Xaa^{64}$ is Tyr or Leu, provided that at least one of $Xaa^{63}$ and $Xaa^{64}$ is Tyr.

15. A DNA comprising a nucleotide sequence encoding the hirudin analog of claim 14.

16. A hirudin analog expression vector having a nucleotide sequence comprising the DNA of claim 15.

17. A recombinant microorganism comprising the expression vector of claim 16.

18. A method of manufacture of a hirudin analog comprising the steps of:

culturing the recombinant microorganism of claim 17 under conditions which permit hirudin production; and harvesting the hirudin analog produced by said microorganism.

19. A composition having anticoagulant properties comprising:

the hirudin analog of claim 14; and a pharmaceutically suitable carrier wherein the hirudin analog is present at a concentration effective for anti-thrombin activity.

* * * * *

SEQUENCE LISTING

<160> NUMBER OF SEQ ID NOS: 29

<210> SEQ ID NO 1
<211> LENGTH: 66
<212> TYPE: PRT
<213> ORGANISM: Artificial Sequence
<220> FEATURE:
<223> OTHER INFORMATION: Description of Artificial Sequence: Artificial
      hirudin sequence
<220> FEATURE:
<221> NAME/KEY: VARIANT
<222> LOCATION: (1)
<223> OTHER INFORMATION: Xaa at position 1 is either Val or Ile
<220> FEATURE:
<221> NAME/KEY: VARIANT
<222> LOCATION: (2)
<223> OTHER INFORMATION: Xaa at position 2 is either Val or Ile
<220> FEATURE:
<221> NAME/KEY: VARIANT
<222> LOCATION: (27)
<223> OTHER INFORMATION: Xaa at position 27 is either Lys or Glu
<220> FEATURE:
<221> NAME/KEY: VARIANT
<222> LOCATION: (33)
<223> OTHER INFORMATION: Xaa at position 33 is either Asp or Asn or Gln
<220> FEATURE:
<221> NAME/KEY: VARIANT
<222> LOCATION: (34)
<223> OTHER INFORMATION: Xaa at position 34 is either Ala or Gly
<220> FEATURE:
<221> NAME/KEY: VARIANT
<222> LOCATION: (35)
<223> OTHER INFORMATION: Xaa at position 35 is either Glu or Lys
<220> FEATURE:
<221> NAME/KEY: VARIANT
<222> LOCATION: (36)
<223> OTHER INFORMATION: Xaa at position 36 is either Lys or Asp
<220> FEATURE:
<221> NAME/KEY: VARIANT
<222> LOCATION: (62)
<223> OTHER INFORMATION: Xaa at position 62 is either Asp or Glu
<220> FEATURE:
<221> NAME/KEY: VARIANT
<222> LOCATION: (63)
<223> OTHER INFORMATION: Xaa at position 63 is either present or not
      present.  When present, Xaa at position 63 is
      either Ala or Tyr.
<220> FEATURE:
<221> NAME/KEY: VARIANT
<222> LOCATION: (64)
<223> OTHER INFORMATION: Xaa at position 64 is either Tyr or Leu
<220> FEATURE:
<221> NAME/KEY: VARIANT
<222> LOCATION: (63)..(64)
<223> OTHER INFORMATION: at least one of Xaa at position 63 and Xaa at
      position 64 is always Tyr

<400> SEQUENCE: 1

Xaa Xaa Tyr Thr Asp Cys Thr Glu Ser Gly Gln Asn Leu Cys Leu Cys
 1               5                  10                  15

Glu Gly Ser Asn Val Cys Gly Gln Gly Asn Xaa Cys Ile Leu Gly Ser
             20                  25                  30

Xaa Xaa Xaa Xaa Asn Gln Cys Val Thr Gly Glu Gly Thr Pro Lys Pro
         35                  40                  45

Gln Ser His Asn Gln Gly Asp Phe Glu Pro Ile Pro Glu Xaa Xaa Xaa
     50                  55                  60

Asp Glu
 65

<210> SEQ ID NO 2
<211> LENGTH: 198

```
<212> TYPE: DNA
<213> ORGANISM: Artificial Sequence
<220> FEATURE:
<223> OTHER INFORMATION: Description of Artificial Sequence: Artificial
      hirudin sequence
<220> FEATURE:
<221> NAME/KEY: variation
<222> LOCATION: (97)..(99)
<223> OTHER INFORMATION: nnn at position 97-99 is gat or aac or cag
<220> FEATURE:
<221> NAME/KEY: variation
<222> LOCATION: (100)..(102)
<223> OTHER INFORMATION: nnn at position 100-102 is gct or ggt
<220> FEATURE:
<221> NAME/KEY: variation
<222> LOCATION: (103)..(105)
<223> OTHER INFORMATION: nnn at position 103-105 is gaa or aaa
<220> FEATURE:
<221> NAME/KEY: variation
<222> LOCATION: (106)..(108)
<223> OTHER INFORMATION: nnn at position 106-108 is aag or gat
<220> FEATURE:
<221> NAME/KEY: variation
<222> LOCATION: (184)..(186)
<223> OTHER INFORMATION: nnn at position 184-186 is gac or gaa
<220> FEATURE:
<221> NAME/KEY: variation
<222> LOCATION: (187)..(189)
<223> OTHER INFORMATION: nnn at position 187-189 is either present or not
      present.  When present, nnn at position 187-189
      is either gcg or tac.
<220> FEATURE:
<221> NAME/KEY: variation
<222> LOCATION: (190)..(192)
<223> OTHER INFORMATION: nnn at position 190-192 is tac or ctg

<400> SEQUENCE: 2
gttgtataca ctgattgtac tgaatctggc cagaacctgt gtctgtgtga aggatccaac      60
gtttgtggtc agggtaacaa atgtatcctc gggtctnnnn nnnnnnnnaa ccagtgtgtt     120
actggtgaag gtaccccgaa accgcagtct cataaccagg gtgatttcga accgatcccg     180
gaannnnnnn nngatgaa                                                   198

<210> SEQ ID NO 3
<211> LENGTH: 198
<212> TYPE: DNA
<213> ORGANISM: Artificial Sequence
<220> FEATURE:
<223> OTHER INFORMATION: Description of Artificial Sequence: Artificial
      hirudin sequence
<220> FEATURE:
<221> NAME/KEY: variation
<222> LOCATION: (79)..(81)
<223> OTHER INFORMATION: nnn at position 79-81 is aaa or gaa

<400> SEQUENCE: 3
atcatctaca ctgattgtac tgaatctggc cagaacctgt gtctgtgtga aggatccaac      60
gtttgtggtc agggtaacnn ntgtatcctc gggtctgatg gtgaaaagaa ccagtgtgtt     120
actggtgaag gtaccccgaa accgcagtct cataaccagg gtgatttcga accgatcccg     180
gaagacgcgt acgatgaa                                                   198

<210> SEQ ID NO 4
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide DA-1
<220> FEATURE:
<221> NAME/KEY: CDS
<222> LOCATION: (3)..(44)
```

<400> SEQUENCE: 4

```
tc ggg tct gat gct gaa aag aac cag tgt gtt act ggt gaa ggt ac        46
   Gly Ser Asp Ala Glu Lys Asn Gln Cys Val Thr Gly Glu Gly
    1               5                  10
```

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Translation of nucleotides
      3-44 of synthetic oligonucleotide DA-1

<400> SEQUENCE: 5

```
Gly Ser Asp Ala Glu Lys Asn Gln Cys Val Thr Gly Glu Gly
 1               5                  10
```

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide DA-2

<400> SEQUENCE: 6

```
cttcaccagt aacacactgg ttcttttcag catcagac                            38
```

<210> SEQ ID NO 7
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide NA-1
<220> FEATURE:
<221> NAME/KEY: CDS
<222> LOCATION: (3)..(44)

<400> SEQUENCE: 7

```
tc ggg tct aac gct gaa aag aac cag tgt gtt act ggt gaa ggt ac        46
   Gly Ser Asn Ala Glu Lys Asn Gln Cys Val Thr Gly Glu Gly
    1               5                  10
```

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Translation of nucleotides
      3-44 of synthetic oligonucleotide NA-1

<400> SEQUENCE: 8

```
Gly Ser Asn Ala Glu Lys Asn Gln Cys Val Thr Gly Glu Gly
 1               5                  10
```

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide NA-2

<400> SEQUENCE: 9

```
cttcaccagt aacacactgg ttcttttcag cgttagac                            38
```

```
<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide 1-1
<220> FEATURE:
<221> NAME/KEY: CDS
<222> LOCATION: (2)..(34)

<400> SEQUENCE: 10 c ccg aaa ccg cag tct cat aac cag ggt gat ttc                    34
  Pro Lys Pro Gln Ser His Asn Gln Gly Asp Phe
   1               5                  10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Translation
      of nucleotides 2-34 of synthetic oligonucleotide 1-1

<400> SEQUENCE: 11

Pro Lys Pro Gln Ser His Asn Gln Gly Asp Phe
 1               5                  10

<210> SEQ ID NO 12
<211> LENGTH: 34
<212> TYPE: DNA
<213> ORGANISM: Artificial Sequence
<220> FEATURE:
<221> NAME/KEY: CDS
<222> LOCATION: (1)..(30)
<220> FEATURE:
<223> OTHER INFORMATION: Description of Artificial Sequence: Synthetic
      oligonucleotide 1-2

<400> SEQUENCE: 12 gaa ccg atc ccg gaa gaa gcg tac gat gaa taaa                     34
Glu Pro Ile Pro Glu Glu Ala Tyr Asp Glu
 1               5                  10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Translation
      of nucleotides 1-30 of synthetic oligonucleotide 1-2

<400> SEQUENCE: 13

Glu Pro Ile Pro Glu Glu Ala Tyr Asp Glu
 1               5                  10

<210> SEQ ID NO 14
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide 1-3

<400> SEQUENCE: 14
gatcggttcg aaatcaccct ggttatgaga ctgcggtttc ggggtac                47

<210> SEQ ID NO 15
<211> LENGTH: 29
<212> TYPE: DNA
```

```
<213> ORGANISM: Artificial Sequence
<220> FEATURE:
<223> OTHER INFORMATION: Description of Artificial Sequence: Synthetic
      oligonucleotide 1-4

<400> SEQUENCE: 15
agcttttatt catcgtacgc ttcttccgg                                    29

<210> SEQ ID NO 16
<211> LENGTH: 34
<212> TYPE: DNA
<213> ORGANISM: Artificial Sequence
<220> FEATURE:
<221> NAME/KEY: CDS
<222> LOCATION: (2)..(34)
<220> FEATURE:
<223> OTHER INFORMATION: Description of Artificial Sequence: Synthetic
      oligonucleotide 2-1

<400> SEQUENCE: 16 c ccg aaa ccg cag tct cat aac cag ggt gat ttc                      34
  Pro Lys Pro Gln Ser His Asn Gln Gly Asp Phe
   1               5                  10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Translation
      of nucleotides 2-34 of synthetic oligonucleotide 2-1

<400> SEQUENCE: 17

Pro Lys Pro Gln Ser His Asn Gln Gly Asp Phe
 1               5                  10

<210> SEQ ID NO 18
<211> LENGTH: 31
<212> TYPE: DNA
<213> ORGANISM: Artificial Sequence
<220> FEATURE:
<221> NAME/KEY: CDS
<222> LOCATION: (1)..(27)
<220> FEATURE:
<223> OTHER INFORMATION: Description of Artificial Sequence: Synthetic
      oligonucleotide 2-2

<400> SEQUENCE: 18 gaa ccg atc ccg gaa gac tac gat gaa taaa                           31
Glu Pro Ile Pro Glu Asp Tyr Asp Glu
 1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Translation
      of nucleotides 1-27 of synthetic oligonucleotide 2-2

<400> SEQUENCE: 19

Glu Pro Ile Pro Glu Asp Tyr Asp Glu
 1               5

<210> SEQ ID NO 20
<211> LENGTH: 47
<212> TYPE: DNA
<213> ORGANISM: Artificial Sequence
<220> FEATURE:
<223> OTHER INFORMATION: Description of Artificial Sequence: Synthetic
```

-continued oligonucleotide 2-3

<400> SEQUENCE: 20
gatcggttcg aaatcaccct ggttatgaga ctgcggtttc ggggtac       47

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide 2-4

<400> SEQUENCE: 21
agcttttatt catcgtagtc ttccgg       26

<210> SEQ ID NO 22
<211> LENGTH: 34
<212> TYPE: DNA
<213> ORGANISM: Artificial Sequence
<220> FEATURE:
<221> NAME/KEY: CDS
<222> LOCATION: (2)..(34)
<220> FEATURE:
<223> OTHER INFORMATION: Description of Artificial Sequence: Synthetic
      oligonucleotide 3-1

<400> SEQUENCE: 22 c ccg aaa ccg cag tct cat aac cag ggt gat ttc       34
  Pro Lys Pro Gln Ser His Asn Gln Gly Asp Phe
  1               5                  10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Translation
      of nucleotides 2-34 of synthetic oligonucleotide 3-1

<400> SEQUENCE: 23

Pro Lys Pro Gln Ser His Asn Gln Gly Asp Phe
1               5                  10

<210> SEQ ID NO 24
<211> LENGTH: 34
<212> TYPE: DNA
<213> ORGANISM: Artificial Sequence
<220> FEATURE:
<221> NAME/KEY: CDS
<222> LOCATION: (1)..(30)
<220> FEATURE:
<223> OTHER INFORMATION: Description of Artificial Sequence: Synthetic
      oligonucleotide 3-2

<400> SEQUENCE: 24 gaa ccg atc ccg gaa gac tac ctg gac gaa taaa       34
Glu Pro Ile Pro Glu Asp Tyr Leu Asp Glu
1               5                  10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Translation
      of nucleotides 1-30 of synthetic oligonucleotide 3-2

<400> SEQUENCE: 25

```
Glu Pro Ile Pro Glu Asp Tyr Leu Asp Glu
 1               5                  10
```

<210> SEQ ID NO 26
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide 3-3

<400> SEQUENCE: 26
gatcggttcg aaatcaccct ggttatgaga ctgcggtttc ggggtac          47

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide 3-4

<400> SEQUENCE: 27
agcttttatt cgtccaggta gtcttccgg                              29

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      mutagen primer 1

<400> SEQUENCE: 28
accaaagcta tcatctacac tgat                                   24

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      mutagen primer 2

<400> SEQUENCE: 29
cagggtaacg aatgtatcct c                                      21